(12) United States Patent
Hunter et al.

(10) Patent No.: US 9,517,030 B2
(45) Date of Patent: *Dec. 13, 2016

(54) NONLINEAR SYSTEM IDENTIFICATION TECHNIQUES AND DEVICES FOR DISCOVERING DYNAMIC AND STATIC TISSUE PROPERTIES

(71) Applicant: Massachusetts Institute of Technology, Cambridge, MA (US)

(72) Inventors: Ian W. Hunter, Lincoln, MA (US); Yi Chen, St. Charles, MO (US)

(73) Assignee: Massachusetts Institute of Technology, Cambridge, MA (US)

( * ) Notice: Subject to any disclaimer, the term of this patent is extended or adjusted under 35 U.S.C. 154(b) by 63 days.

This patent is subject to a terminal disclaimer.

(21) Appl. No.: 14/310,744

(22) Filed: Jun. 20, 2014

(65) Prior Publication Data

US 2015/0051513 A1  Feb. 19, 2015

Related U.S. Application Data

(63) Continuation of application No. 12/872,630, filed on Aug. 31, 2010, now Pat. No. 8,758,271.

(Continued)

(51) Int. Cl.
*A61B 5/00* (2006.01)
*A01G 7/00* (2006.01)
(Continued)

(52) U.S. Cl.
CPC ............ *A61B 5/442* (2013.01); *A01G 7/00* (2013.01); *A61B 5/0048* (2013.01);
(Continued)

(58) Field of Classification Search
CPC .............................. A61B 5/442; A61B 5/0057
See application file for complete search history.

(56) References Cited

U.S. PATENT DOCUMENTS

| 2,194,535 A | 3/1940 | von Delden |
| 2,550,053 A | 4/1951 | Ferguson |

(Continued)

FOREIGN PATENT DOCUMENTS

| DE | 201 05 183 U1 | 6/2002 |
| DE | 101 46 535 A | 4/2003 |

(Continued)

OTHER PUBLICATIONS

Marmarelis, V. Z. "Methods and Tools for Identification of Physiologic Systems," in Bronzino, J.D. (Ed.), Biomechanical Engineering Fundamentals, pp. 13-1 to 13-15 (no date given).

(Continued)

*Primary Examiner* — Michael C Stout
*Assistant Examiner* — Nicholas E Kolderman
(74) *Attorney, Agent, or Firm* — Hamilton, Brook, Smith & Reynolds, P.C.

(57) ABSTRACT

A device for measuring a mechanical property of a tissue includes a probe configured to perturb the tissue with movement relative to a surface of the tissue, an actuator coupled to the probe to move the probe, a detector configured to measure a response of the tissue to the perturbation, and a controller coupled to the actuator and the detector. The controller drives the actuator using a stochastic sequence and determines the mechanical property of the tissue using the measured response received from the detector. The probe can be coupled to the tissue surface. The device can include a reference surface configured to contact the tissue surface. The probe may include a set of interchangeable heads, the set including a head for lateral movement of the probe and a head for perpendicular movement of the probe. The perturbation can include extension of the tissue with the probe or sliding the probe across the tissue surface and may also include indentation of the tissue with the probe. In some (Continued)

embodiments, the actuator includes a Lorentz force linear actuator. The mechanical property may be determined using non-linear stochastic system identification. The mechanical property may be indicative of, for example, tissue compliance and tissue elasticity. The device can further include a handle for manual application of the probe to the surface of the tissue and may include an accelerometer detecting an orientation of the probe. The device can be used to test skin tissue of an animal, plant tissue, such as fruit and vegetables, or any other biological tissue.

11 Claims, 21 Drawing Sheets

Related U.S. Application Data

(60) Provisional application No. 61/238,832, filed on Sep. 1, 2009, provisional application No. 61/238,866, filed on Sep. 1, 2009, provisional application No. 61/371,150, filed on Aug. 5, 2010.

(51) Int. Cl.
 G01N 3/24 (2006.01)
 G01N 3/40 (2006.01)
 A61B 9/00 (2006.01)

(52) U.S. Cl.
 CPC .......... A61B 5/0053 (2013.01); A61B 5/0055 (2013.01); A61B 5/0057 (2013.01); A61B 9/00 (2013.01); G01N 3/24 (2013.01); G01N 3/40 (2013.01); A61B 5/6824 (2013.01); G01N 2203/0069 (2013.01); G01N 2203/0218 (2013.01); G01N 2203/0246 (2013.01); G01N 2203/0278 (2013.01)

(56) References Cited

U.S. PATENT DOCUMENTS

| | | |
|---|---|---|
| 2,754,818 A | 7/1956 | Scherer |
| 2,928,390 A | 3/1960 | Venditty et al. |
| 3,057,349 A | 10/1962 | Ismach |
| 3,309,274 A | 3/1967 | Brilliant |
| 3,574,431 A | 4/1971 | Henderson |
| 3,624,219 A | 11/1971 | Perlitsh |
| 3,659,600 A | 5/1972 | Merrill |
| 3,788,315 A | 1/1974 | Laurens |
| 3,810,465 A | 5/1974 | Lambert |
| 3,815,594 A | 6/1974 | Doherty |
| 3,923,060 A | 12/1975 | Ellinwood, Jr. |
| 3,973,558 A | 8/1976 | Stouffer et al. |
| 3,977,402 A | 8/1976 | Pike |
| 4,071,956 A | 2/1978 | Andress |
| 4,097,604 A | 6/1978 | Thiele |
| 4,103,684 A | 8/1978 | Ismach |
| 4,108,177 A | 8/1978 | Pistor |
| 4,122,845 A | 10/1978 | Stouffer et al. |
| 4,206,769 A | 6/1980 | Dikstein |
| 4,214,006 A | 7/1980 | Thiele |
| 4,215,144 A | 7/1980 | Thiele |
| 4,348,378 A | 9/1982 | Kosti |
| 4,431,628 A | 2/1984 | Gaffar |
| 4,435,173 A | 3/1984 | Siposs et al. |
| 4,447,225 A | 5/1984 | Taff et al. |
| 4,552,559 A | 11/1985 | Donaldson et al. |
| 4,592,742 A | 6/1986 | Landau |
| 4,744,841 A | 5/1988 | Thomas |
| 4,777,599 A | 10/1988 | Dorogi et al. |
| 4,886,499 A | 12/1989 | Cirelli et al. |
| 5,054,502 A | 10/1991 | Courage |
| 5,074,843 A | 12/1991 | Dalto et al. |
| 5,092,901 A | 3/1992 | Hunter et al. |
| 5,116,313 A | 5/1992 | McGregor |
| 5,242,408 A | 9/1993 | Jhuboo et al. |
| 5,244,461 A | 9/1993 | Derlien |
| 5,268,148 A | 12/1993 | Seymour |
| 5,277,200 A | 1/1994 | Kawazoe et al. |
| 5,318,522 A | 6/1994 | D'Antonio |
| 5,347,186 A | 9/1994 | Konotchick |
| 5,354,273 A | 10/1994 | Hagen |
| 5,389,085 A | 2/1995 | D'Alessio et al. |
| 5,405,614 A | 4/1995 | D'Angelo et al. |
| 5,425,715 A | 6/1995 | Dalling et al. |
| 5,478,328 A | 12/1995 | Silverman et al. |
| 5,479,937 A | 1/1996 | Thieme et al. |
| 5,480,381 A | 1/1996 | Weston |
| 5,505,697 A | 4/1996 | McKinnon, Jr. et al. |
| 5,533,995 A | 7/1996 | Corish et al. |
| 5,578,495 A | 11/1996 | Wilks |
| 5,611,784 A | 3/1997 | Barresi et al. |
| 5,622,482 A | 4/1997 | Lee |
| 5,694,920 A | 12/1997 | Abrams et al. |
| 5,722,953 A | 3/1998 | Schiff et al. |
| 5,795,153 A | 8/1998 | Rechmann |
| 5,820,373 A | 10/1998 | Okano et al. |
| 5,840,062 A | 11/1998 | Gumaste et al. |
| 5,865,795 A | 2/1999 | Schiff et al. |
| 5,879,312 A | 3/1999 | Imoto |
| 5,879,327 A | 3/1999 | Moreau DeFarges et al. |
| 5,919,167 A | 7/1999 | Mulhauser et al. |
| 6,004,287 A | 12/1999 | Loomis et al. |
| 6,030,399 A | 2/2000 | Ignotz et al. |
| 6,037,682 A | 3/2000 | Shoop et al. |
| 6,048,337 A | 4/2000 | Svedman |
| 6,056,716 A | 5/2000 | D'Antonio et al. |
| 6,074,360 A | 6/2000 | Haar et al. |
| 6,090,790 A | 7/2000 | Eriksson |
| 6,123,684 A | 9/2000 | Deboer et al. |
| 6,126,629 A | 10/2000 | Perkins |
| 6,132,385 A | 10/2000 | Vain |
| 6,152,887 A | 11/2000 | Blume |
| 6,155,824 A | 12/2000 | Kamen et al. |
| 6,164,966 A | 12/2000 | Turdiu et al. |
| 6,203,521 B1 | 3/2001 | Menne et al. |
| 6,258,062 B1 | 7/2001 | Thielen et al. |
| 6,272,857 B1 | 8/2001 | Varma |
| 6,288,519 B1 | 9/2001 | Peele |
| 6,317,630 B1 | 11/2001 | Gross et al. |
| 6,319,230 B1 | 11/2001 | Palasis et al. |
| 6,375,624 B1 | 4/2002 | Uber, III et al. |
| 6,375,638 B2 | 4/2002 | Nason et al. |
| 6,408,204 B1 | 6/2002 | Hirschman |
| 6,485,300 B1 | 11/2002 | Muller et al. |
| 6,565,532 B1 | 5/2003 | Yuzhakov et al. |
| 6,611,707 B1 | 8/2003 | Prausnitz et al. |
| 6,626,871 B1 | 9/2003 | Smoliarov et al. |
| 6,656,159 B2 | 12/2003 | Flaherty |
| 6,673,033 B1 | 1/2004 | Sciulli et al. |
| 6,678,556 B1 | 1/2004 | Nolan et al. |
| 6,723,072 B2 | 4/2004 | Mahoney et al. |
| 6,743,211 B1 | 6/2004 | Prausnitz et al. |
| 6,770,054 B1 | 8/2004 | Smolyarov et al. |
| 6,939,323 B2 | 9/2005 | Angel et al. |
| 7,032,443 B2 | 4/2006 | Moser |
| 7,066,922 B2 | 6/2006 | Angel et al. |
| 7,270,543 B2 | 9/2007 | Stookey et al. |
| 7,344,498 B1 | 3/2008 | Doughty et al. |
| 7,364,568 B2 | 4/2008 | Angel et al. |
| 7,425,204 B2 | 9/2008 | Angel et al. |
| 7,429,258 B2 | 9/2008 | Angel et al. |
| 7,530,975 B2 | 5/2009 | Hunter |
| 7,645,263 B2 | 1/2010 | Angel et al. |
| 7,651,475 B2 | 1/2010 | Angel et al. |
| 7,833,189 B2 | 11/2010 | Hunter et al. |
| 7,916,282 B2 | 3/2011 | Duineveld et al. |
| 8,105,270 B2 | 1/2012 | Hunter |
| 8,172,790 B2 | 5/2012 | Hunter et al. |
| 8,246,582 B2 | 8/2012 | Angel et al. |
| 8,328,755 B2 | 12/2012 | Hunter et al. |
| 8,398,583 B2 | 3/2013 | Hunter et al. |
| 8,740,838 B2 | 6/2014 | Hemond et al. |

(56) References Cited

U.S. PATENT DOCUMENTS

| | | |
|---|---|---|
| 8,758,271 B2 * | 6/2014 | Hunter ................ A01G 7/00 600/587 |
| 8,821,434 B2 | 9/2014 | Hunter et al. |
| 8,992,466 B2 | 3/2015 | Hunter et al. |
| 9,265,461 B2 | 2/2016 | Hunter et al. |
| 9,308,326 B2 | 4/2016 | Hunter et al. |
| 9,333,060 B2 | 5/2016 | Hunter et al. |
| 2002/0029924 A1 | 3/2002 | Courage |
| 2002/0055552 A1 | 5/2002 | Schliesman et al. |
| 2002/0055729 A1 | 5/2002 | Goll |
| 2002/0095124 A1 | 7/2002 | Palasis et al. |
| 2002/0145364 A1 | 10/2002 | Gaide et al. |
| 2003/0065306 A1 | 4/2003 | Grund |
| 2003/0073931 A1 | 4/2003 | Boecker et al. |
| 2003/0083618 A1 | 5/2003 | Angel et al. |
| 2003/0083645 A1 | 5/2003 | Angel et al. |
| 2003/0153844 A1 | 8/2003 | Smith et al. |
| 2003/0207232 A1 | 11/2003 | Todd et al. |
| 2004/0010207 A1 | 1/2004 | Flaherty et al. |
| 2004/0024364 A1 | 2/2004 | Langley et al. |
| 2004/0065170 A1 | 4/2004 | Wu et al. |
| 2004/0094146 A1 | 5/2004 | Schiewe et al. |
| 2004/0106893 A1 * | 6/2004 | Hunter ................ A61B 5/0051 604/66 |
| 2004/0106894 A1 | 6/2004 | Hunter et al. |
| 2004/0143213 A1 | 7/2004 | Hunter et al. |
| 2004/0260234 A1 | 12/2004 | Srinivasan et al. |
| 2005/0022806 A1 | 2/2005 | Beaumont et al. |
| 2005/0170316 A1 | 8/2005 | Russell et al. |
| 2005/0287490 A1 | 12/2005 | Stookey et al. |
| 2006/0115785 A1 | 6/2006 | Li et al. |
| 2006/0184101 A1 | 8/2006 | Srinivasan et al. |
| 2006/0258986 A1 | 11/2006 | Hunter et al. |
| 2007/0052139 A1 | 3/2007 | Gilbert |
| 2007/0055200 A1 | 3/2007 | Gilbert |
| 2007/0093712 A1 | 4/2007 | Nemoto et al. |
| 2007/0111166 A1 | 5/2007 | Dursi |
| 2007/0129693 A1 | 6/2007 | Hunter et al. |
| 2007/0154863 A1 | 7/2007 | Cai et al. |
| 2007/0191758 A1 | 8/2007 | Hunter et al. |
| 2007/0248932 A1 | 10/2007 | Gharib et al. |
| 2007/0275347 A1 | 11/2007 | Gruber |
| 2008/0009788 A1 | 1/2008 | Hunter et al. |
| 2008/0027575 A1 | 1/2008 | Jones et al. |
| 2008/0060148 A1 | 3/2008 | Pinyayev et al. |
| 2008/0126129 A1 | 5/2008 | Manzo |
| 2008/0152694 A1 | 6/2008 | Lobl et al. |
| 2008/0183101 A1 | 7/2008 | Stonehouse et al. |
| 2008/0281273 A1 | 11/2008 | Angel et al. |
| 2009/0017423 A1 | 1/2009 | Gottenbos et al. |
| 2009/0030285 A1 | 1/2009 | Andersen |
| 2009/0056427 A1 | 3/2009 | Hansma et al. |
| 2009/0081607 A1 | 3/2009 | Frey |
| 2009/0221986 A1 | 9/2009 | Wang et al. |
| 2009/0240230 A1 | 9/2009 | Azar et al. |
| 2010/0004624 A1 | 1/2010 | Hunter |
| 2010/0143861 A1 | 6/2010 | Gharib et al. |
| 2010/0160897 A1 | 6/2010 | Ducharme et al. |
| 2011/0009821 A1 | 1/2011 | Jespersen et al. |
| 2011/0054354 A1 | 3/2011 | Hunter et al. |
| 2011/0054355 A1 | 3/2011 | Hunter et al. |
| 2011/0143310 A1 | 6/2011 | Hunter |
| 2011/0166549 A1 | 7/2011 | Hunter et al. |
| 2011/0224603 A1 | 9/2011 | Richter |
| 2011/0270216 A1 | 11/2011 | Rykhus et al. |
| 2011/0311939 A1 | 12/2011 | Hunter |
| 2012/0003601 A1 | 1/2012 | Hunter et al. |
| 2012/0089114 A1 | 4/2012 | Hemond et al. |
| 2012/0095435 A1 | 4/2012 | Hunter et al. |
| 2012/0116212 A1 | 5/2012 | Bral |
| 2013/0102957 A1 | 4/2013 | Hunter et al. |
| 2014/0257236 A1 | 9/2014 | Hemond et al. |
| 2015/0005701 A1 | 1/2015 | Hunter et al. |
| 2015/0025505 A1 | 1/2015 | Hunter et al. |
| 2016/0197542 A1 | 7/2016 | Hunter et al. |

FOREIGN PATENT DOCUMENTS

| | | |
|---|---|---|
| EP | 0 599 940 B1 | 12/1997 |
| EP | 0 834 330 A2 | 4/1998 |
| EP | 1 020 200 A2 | 7/2000 |
| EP | 0 710 130 B1 | 12/2000 |
| EP | 1 514 565 A1 | 3/2005 |
| GB | 686343 | 1/1953 |
| GB | 756957 | 9/1956 |
| GB | 2307860 A | 6/1997 |
| JP | 04-500166 A | 1/1992 |
| JP | 06-327639 A | 11/1994 |
| JP | 10-314122 A | 12/1998 |
| JP | 2001-046344 A | 2/2001 |
| JP | 2001-212087 A | 8/2001 |
| JP | 2002-511776 | 4/2002 |
| JP | 2004-085548 A | 3/2004 |
| JP | 2004-239686 A | 8/2004 |
| JP | 2005-87722 | 4/2005 |
| JP | 2005-521538 A | 7/2005 |
| JP | 2005-5376834 A | 12/2005 |
| JP | 2007-044531 A | 2/2007 |
| JP | 2008-529677 A | 8/2008 |
| JP | 2009-520570 A | 5/2009 |
| JP | 2010-502290 A | 1/2010 |
| JP | 5284962 B | 6/2013 |
| WO | WO 90/01961 | 3/1990 |
| WO | WO 91/16003 A1 | 10/1991 |
| WO | WO 93/03779 A1 | 3/1993 |
| WO | WO 95/07722 A1 | 3/1995 |
| WO | WO 98/08073 A1 | 2/1998 |
| WO | WO 98/17332 | 4/1998 |
| WO | WO 00/23132 A1 | 4/2000 |
| WO | WO 01/26716 A1 | 4/2001 |
| WO | WO 01/37907 A1 | 5/2001 |
| WO | WO 02/00469 A1 | 12/2002 |
| WO | WO 03/035149 A1 | 5/2003 |
| WO | WO 03/037403 | 5/2003 |
| WO | WO 03/037404 | 5/2003 |
| WO | WO 03/037405 | 5/2003 |
| WO | WO 03/037406 | 5/2003 |
| WO | WO 03/037407 | 5/2003 |
| WO | WO 03/039635 A2 | 5/2003 |
| WO | WO 03/068296 A2 | 8/2003 |
| WO | WO 03/086510 A1 | 10/2003 |
| WO | WO 2004/021882 A2 | 3/2004 |
| WO | WO 2004/022138 A2 | 3/2004 |
| WO | WO 2004/022244 | 3/2004 |
| WO | WO 2004/093818 A2 | 4/2004 |
| WO | WO 2004/058066 A1 | 7/2004 |
| WO | WO 2004/071936 A2 | 8/2004 |
| WO | WO 2004/101025 A2 | 11/2004 |
| WO | WO 2004/112871 A1 | 12/2004 |
| WO | WO 2006/086719 | 8/2006 |
| WO | WO 2006/086720 A2 | 8/2006 |
| WO | WO 2006/086774 A2 | 8/2006 |
| WO | WO 2007/058966 | 5/2007 |
| WO | WO 2007/061896 A1 | 5/2007 |
| WO | WO 2008/001303 A1 | 1/2008 |
| WO | WO 2008/001377 | 1/2008 |
| WO | WO 2008/027579 A1 | 3/2008 |
| WO | WO 2010/031424 A1 | 3/2010 |
| WO | WO 2010/077271 A1 | 7/2010 |
| WO | WO 2011/028716 A1 | 3/2011 |
| WO | WO 2011/028719 A2 | 3/2011 |
| WO | WO 2011/075535 A1 | 6/2011 |
| WO | WO 2011/075545 A1 | 6/2011 |
| WO | WO 2011/084511 A1 | 7/2011 |
| WO | WO 2012/048268 A2 | 4/2012 |
| WO | WO 2012/048277 A2 | 4/2012 |

OTHER PUBLICATIONS

Hemond, B.D., et al., "Development and Performance of a Controllable Autoloading Needle-Free Jet Injector", *J. Med. Dev.*, Mar. 2011, vol. 5, pp. 015001-1 through 015001-7.

Stachowiak, J. C., et al., "Dynamic control of needle-free jet injection", *J. Controlled Rel.*, 135:104-112 (2009).

(56) References Cited

OTHER PUBLICATIONS

Taberner, et al., "Needle-free jet injection using real-time controlled linear Lorentz-force actuators," *Med. Eng. Phys.*, (2012) doi: 10.1016/j.medengphy.2011.12.010.
Non-Final Office Action for U.S. Appl. No. 12/872,643, entitled "Identification Techniques and Device for Testing the Efficacy of Beauty Care Products and Cosmetics", Dated: Mar. 13, 2015.
Bischoff, J. E., et al., "Finite element modeling of human skin using an isotropic, nonlinear elastic constitutive model," *J. Biomech.*, 33: 645-652 (2000).
Boyer, G., et al., "Dynamic indentation on human skin in vivo: ageing effects," *Skin Research and Technology*, 15: 55-67 (2009).
Carter, F. J., et al., "Measurements and modelling of the compliance of human and porcine organs," *Medical Image Analysis*, 5: 231-236 (2001).
Chen, K., et al., "A Needle-free Liquid Injection System Powered by Lorentz-force Actuator." Paper presented at International Conference on Mechanic Automation and Control Engineering, Wuhan, China (Jun. 2010).
Chen, K., and Zhou, H., "An experimental study and model validation of pressure in liquid needle-free injection," *International Journal of the Physical Sciences*, 6(7): 1552-1562 (2011).
Chen, Y., and Hunter, I. W., "In Vivo Characterization of Skin using a Wiener Nonlinear Stochastic System Identification Method," *Proceedings of the 31st IEEE EMBS Annual International Conference*, 6010-6013 (2009).
Chen, Y., and Hunter, I. W., "Nonlinear Stochastic System Identification of Skin Using Volterra Kernels," *Annals of Biomedical Engineering*, 41(4): 847-862 (2013).
Chen, Y., and Hunter, I. W., "Stochastic System Identification of Skin Properties: Linear and Wiener Static Nonlinear Methods," *Annals of Biomedical Engineering*, 40(10): 2277-2291 (2012).
Daly, C. H., and Odland, G. F., "Age-related Changes in the Mechanical Properties of Human Skin," *The Journal of Investigative Dermatology*, 73: 84-87 (1979).
Delalleau, A., et al., "A nonlinear elastic behavior to identify the mechanical parameters of human skin in vivo," *Skin Research and Technology*, 14: 152-164 (2008).
Diridollou, S., et al., "An In Vivo Method for Measuring the Mechanical Properties of the Skin Using Ultrasound," *Ultrasound in Med. & Biol.*, 24(2): 215-224 (1998).
Diridollou, S., et al., "Sex- and site-dependent variations in the thickness and mechanical properties of human skin in vivo," *Int. J. Cosmetic Sci.*, 22: 421-435 (2000).
Escoffier, C., et al., "Age-Related Mechanical Properties of Human Skin: An In Vivo Study," *J. Invest. Dermatol.*, 93: 353-357 (1989).
Flynn, D. M., et al., "A Finite Element Based Method to Determine the Properties of Planar Soft Tissue," *J. Biomech. Eng.—T. ASME*, 120(2): 202-210 (1998).
Garcia-Webb, M. G., et al., "A modular instrument for exploring the mechanics of cardiac myocytes," *Am. J. Physiol. Heart Circ. Physiol.*, 293: H866-H874 (2007).
Goussard, Y., et al., "Practical Identification of Functional Expansions of Nonlinear Systems Submitted to Non-Gaussian Inputs," *Ann. Biomed. Eng.*, 19: 401-427 (1991).
Hartzshtark, A., and Dikstein, S., "The use of indentometry to study the effect of agents known to increase skin c-AMP content," *Experientia*, 41: 378-379 (1985).
He, M. M., et al., "Two-Exponential Rheological Models of the Mechanical Properties of the Stratum Corneum," *Pharmaceutical Research*, 13(9): S1-S604 (1996).
Hemond, B. D., et al., "A Lorentz-Force Actuated Autoloading Needle-free Injector," *Proceedings of the 28th IEEE EMBS Annual International Conference*, 679-682 (2006).
Hendricks, F. M., et al., "A numerical-experimental method to characterize the non-linear mechanical behaviour of human skin," *Skin Research and Technology*, 9: 274-283 (2003).
Hirota, G., et al., "An Implicit Finite Element Method for Elastic Solids in Contact," *Proceedings on the Fourteenth Conference on Computer Animation*, 136-146 (2001).

Hunter, I. W., and Kearney, R. E., "Generation of Random Sequences with Jointly Specified Probability Density and Autocorrelation Functions," *Biol. Cybern.*, 47: 141-146 (1983).
Hunter, I. W., and Korenberg, M. J., "The Identification of Nonlinear Biological Systems: Wiener and Hammerstein Cascade Models," *Biol. Cybern.*, 55:135-144 (1986).
Jachowicz, J., et al., "Alteration of skin mechanics by thin polymer films," *Skin Research and Technology*, 14: 312-319 (2008).
Khatyr, F., et al., "Model of the viscoelastic behaviour of skin in vivo and study of anisotropy," *Skin Research and Technology*, 10: 96-103 (2004).
Korenberg, M. J., and Hunter, I. W., "The Identification of Nonlinear Biological Systems: LNL Cascade Models," *Biol. Cybern.*, 55: 125-134 (1986).
Korenberg, M. J., and Hunter, I. W., "The identification of Nonlinear Biological Systems: Volterra Kernel Approaches," *Annals of Biomedical Engineering*, 24: 250-268 (1996).
Korenberg, M. J., and Hunter, I. W., "Two Methods for Identifying Wiener Cascades Having Noninvertible Static Nonlinearities," *Annals of Bilmedical Engineeering*, 27: 793-804 (1999).
Lee, Y. W., and Schetzen, M., "Measurement of the Wiener Kernels of a Non-linear System by Cross-correlation," *Int. J. Control*, 2(3): 237-254 (1965).
Lindahl, O. A., et al., "A tactile sensor for detection of physical properties of human skin in vivo," *J. Med. Eng. Technol.*, 22(4): 147-153 (1998).
Lu, M.-H., et al., "A Hand-Held Indentation System for the Assessment of Mechanical Properties of Soft Tissues In Vivo," *IEEE Transactions on Instrumentation and Measurement*, 58(9): 30793085 (2009).
Manschot, J. F. M., and Brakkee, A. J. M., "The Measurement and Modelling of the Mechanical Properties of Human Skin In Vivo—I. The Measurement," *J. Biomech.*, 19(7): 511-515 (1986).
Manschot, J. F. M., and Brakkee, A. J. M., "The Measurement and Modelling of the Mechanical Properties of Human Skin In Vivo—II. The Model," *J. Biomech.*, 19(7): 517-521 (1986).
Menciassi, A., et al., "An Instrumented Probe for Mechanical Characterization of Soft Tissues," *Biomed. Microdevices*, 3(2): 149-156 (2001).
Oka, H., and Irie, T., "Mechanical impedance of layered tissue," *Medical Progress through Technology*, Suppl. 21: 1-4 (1997).
Ottensmeyer, M. P., and Salisbury, J. K., Jr., "In Vivo Data Acquisition Instrument for Solid Organ Mechanical Property Measurement," *Lecture Notes in Computer Science*, 2208: 975-982 (2001).
Patton, R. L., "Mechanical Compliance Transfer Function Analysis for Early Detection of Pressure Ulcers." Bachelor's thesis, Massachusetts Institute of Technology (1999).
Post, E. A., "Portable Sensor to Measure the Mechanical Compliance Transfer Function of a Material." Bachelor's thesis, Massachusetts Institute of Technology (2006).
Potts, R. O., et al., "Changes with Age in the Moisture Content of Human Skin," *The Journal of Investigative Dermatology*, 82(1): 97-100 (1984).
Reihsner, R., et al., "Two-dimensional elastic properties of human skin in terms of an incremental model at the in vivo configuration," *Med. Eng. Phys.*, 17: 304-313 (1995).
Sandford, E., et al., "Capturing skin properties from dynamic mechanical analyses," *Skin Research and Technology*, 0: 1-10 (2012).
Soong, T. T., and Huang, W. N., "A Stochastic Model for Biological Tissue Elasticity," *Proceedings of the Fourth Canadian Congress of Applied Mechanics*, 853-854 (1973).
Tosti, A., et al., "A Ballistometer for the Study of the Plasto-Elastic Properties of Skin," *The Journal of Investigative Dermatology*, 69: 315-317 (1977).
Zahouani, H., et al., "Characterization of the mechanical properties of a dermal equivalent compared with human skin in vivo by indentation and static friction tests," *Skin Research and Technology*, 15: 68-76 (2009).
Zhang, M., and Roberts, V. C., "The effect of shear forces externally applied to skin surface on underlying tissues," *J. Biomed. Eng.*, 15(6): 451-456 (1993).

(56) References Cited

OTHER PUBLICATIONS

International Search Report from International Application No. PCT/US2003/027907, "Measuring Properties of an Anatomical Body," mailed May 6, 2004.
International Search Report from International Application No. PCT/US2003/027909, "Needleless Drug Injection Device," mailed Jun. 15, 2004.
International Preliminary Examination Report from International Application No. PCT/US2003/027909, "Needleless Drug Injection Device," mailed Feb. 21, 2005.
International Preliminary Examination Report from International Application No. PCT/US2003/027907, "Measuring Properties of an Anatomical Body," mailed Feb. 25, 2005.
Partial International Search Report from International Application No. PCT/US2010/047348, "Nonlinear System Identification Techniques and Devices for Discovering Dynamic and Static Tissue Properties," mailed Dec. 17, 2010.
International Search Report and Written Opinion of the International Searching Authority from International Application No. PCT/US2010/047342, "Nonlinear System Identification Technique for Testing the Efficacy of Skin Care Products," mailed Dec. 28, 2010.
International Search Report and Written Opinion of the International Searching Authority from International Application No. PCT/US2010/047348, "Nonlinear System Identification Techniques and Devices for Discovering Dynamic and Static Tissue Properties," mailed Mar. 21, 2011.
International Preliminary Report on Patentability from International Application No. PCT/US2010/047342, "Nonlinear System Identification Technique for Testing the Efficacy of Skin Care Products," mailed Mar. 6, 2012.
International Preliminary Report on Patentability from International Application No. PCT/US2010/047348, "Nonlinear System Identification Techniques and Devices for Discovering Dynamic and Static Tissue Properties," mailed Mar. 6, 2012.
Final Office Action from U.S. Appl. No. 12/872,643, mailed Dec. 26, 2013.
Taberner, A.J., et al., "A Portable Needle-free Jet Injector Based on a Custom High Power-density Voice-coil Actuator", Proceedings of the 28th IEEE, EMBS Annual International Conference, Aug. 30-Sep. 3, 2006, pp. 5001-5004.
Definition "Stream" Merriam-Webster Dictionary http://www.merriam-webster.com/dictionary/stream, p. 1 of 1, dated Jun. 11, 2015.
Definition "Stream" the Free Dictionary http://www.thefreedictionary.com/stream, pp. 1 -8, dated Jun. 11, 2015.

\* cited by examiner

Section A-A

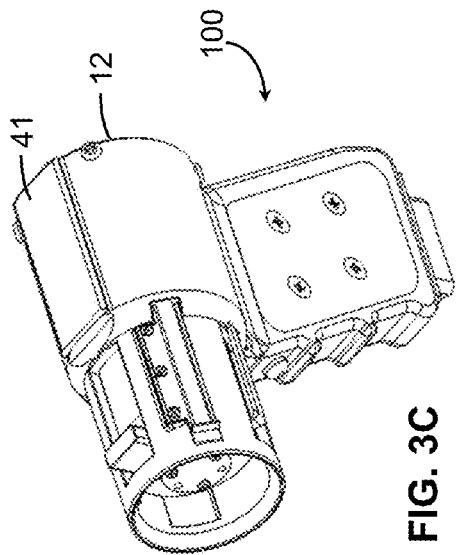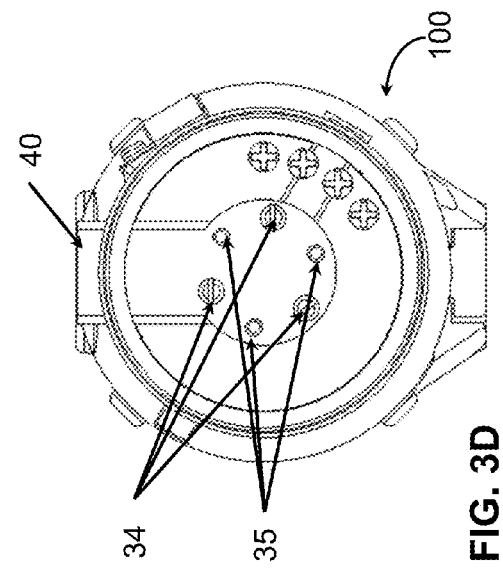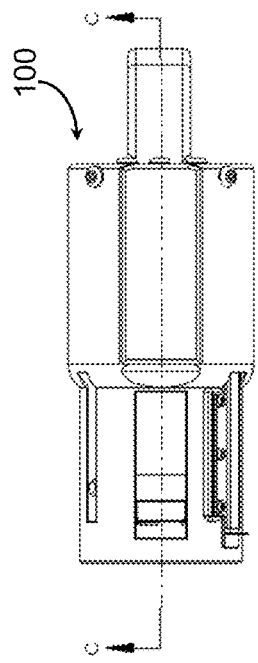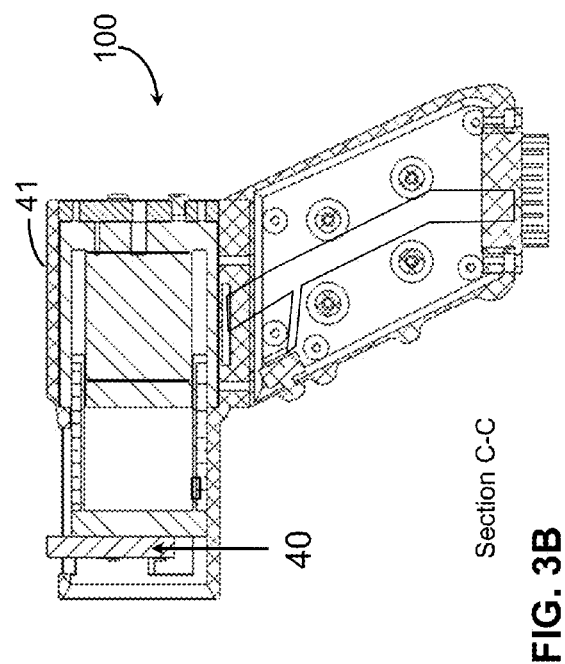

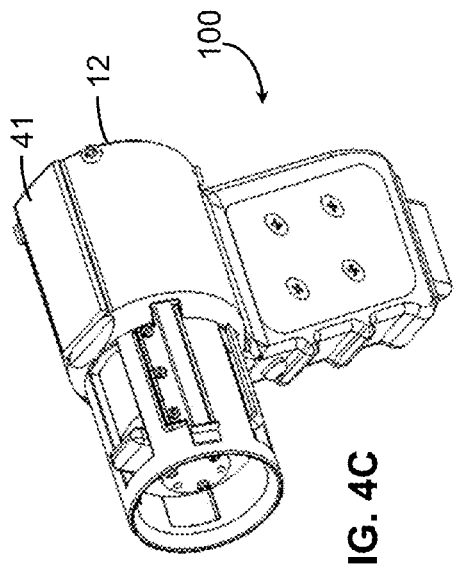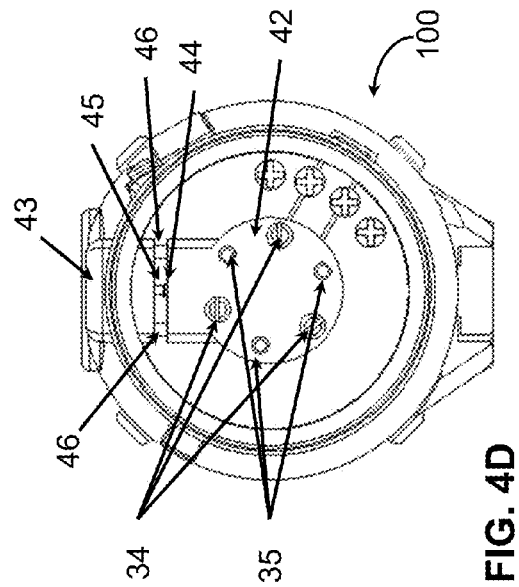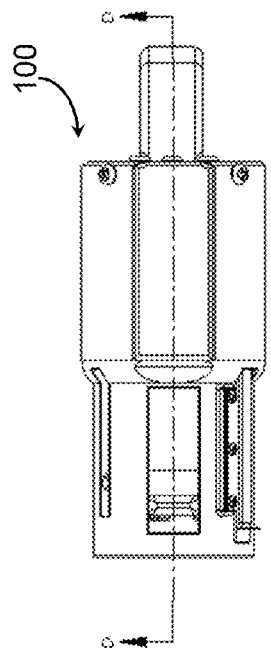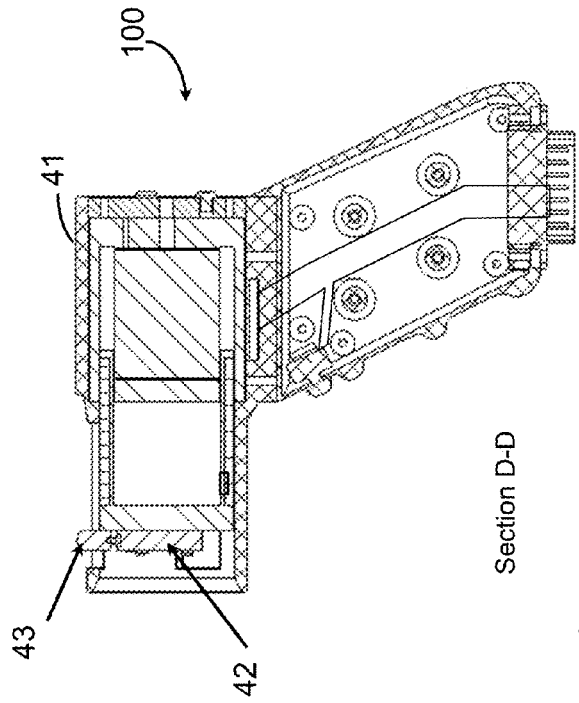

NONLINEAR SYSTEM IDENTIFICATION TECHNIQUES AND DEVICES FOR DISCOVERING DYNAMIC AND STATIC TISSUE PROPERTIES

RELATED APPLICATIONS

This application is a continuation of U.S. application Ser. No. 12/872,630, filed Aug. 31, 2010, which claims the benefit of U.S. Provisional Application No. 61/238,832, filed on Sep. 1, 2009, U.S. Provisional Application No. 61/238,866, filed on Sep. 1, 2009, and U.S. Provisional Application No. 61/371,150 filed on Aug. 5, 2010. The entire teachings of the above applications are incorporated herein by reference.

BACKGROUND OF THE INVENTION

Identifying the mechanical properties of skin and other biological tissues is important for diagnosing healthy from damaged tissue, developing tissue vascularization therapies, and creating injury repair techniques. In addition, the ability to assess the mechanical properties of an individual's skin is essential to cosmetologists and dermatologists in their daily work. Today, the mechanical properties of skin are often assessed qualitatively using touch. This, however, presents a problem in terms of passing information between different individuals or comparing measurements from different clinical studies for the diagnosis of skin conditions.

Studies have explored both the linear and nonlinear properties of biological materials. Testing methods used include suction (S. Diridollou, et al. "An in vivo method for measuring the mechanical properties of the skin using ultrasound," *Ultrasound in Medicine and Biology*, vol. 24, no. 2, pp. 215-224, 1998; F. M. Hendricks, et al., "A numerical—experimental method to characterize the nonlinear mechanical behavior of human skin," *Skin Research and Technology*, vol. 9, pp. 274-283, 2003), torsion (C. Excoffier, et al., "Age-related mechanical properties of human skin: An in vivo study," *Journal of Investigative Dermatology*, vol. 93, pp. 353-357, 1989), extension (F. Khatyr, et al., "Model of the viscoelastic behavior of skin in vivo and study of anisotropy," *Skin Research and Technology*, vol. 10, pp. 96-103, 2004; C. Daly, et al., "Age related changes in the mechanical properties of human skin." *The Journal of Investigative Dermatology*, vol. 73, pp. 84-87, 1979), ballistometry (A. Tosti, et al., "A ballistometer for the study of the plasto-elastic properties of skin," *The Journal of Investigative Dermatology*, vol. 69, pp. 315-317, 1977), and wave propagation (R. O. Potts, et al., "Changes with age in the moisture content of human skin," *The Journal of Investigative Dermatology*, vol. 82, pp. 97-100, 1984).

Commercial devices, such as the CUTOMETER® MPA580, DERMALFLEX, and DIA-STRON brand dermal torque meter, exist for some of these methods. Generally, these devices only provide information about limited aspects of skin behavior which may not be enough to properly diagnose disease. Many of these devices also focus on only linear properties such as skin elasticity.

In another method known as indentometry, (F. J. Carter, et al., "Measurements and modeling of human and porcine organs," *Medical Image Analysis*, vol. 5, pp. 231-236, 2001; M. P. Ottensmeyer, et al., "In vivo data acquisition instrument for solid organ mechanical property measurement," *Lecture Notes in Computer Science*, vol. 2208, pp. 975-982, 2001; G. Boyer, et al., "Dynamic indentation of human skin in vivo: Aging effects," *Skin Research and Technology*, vol. 15, pp. 55-67, 2009) a probe tip is pushed orthogonally into the skin to discover tissue properties. If large enough forces are used, this method is capable of measuring the mechanical properties of not only the epithelial layer, but also the properties of the underlying connective tissue.

The interaction between different tissue layers (C. Daly, et al., "Age related changes in the mechanical properties of human skin." *The Journal of Investigative Dermatology*, vol. 73, pp. 84-87, 1979; H. Oka, et al., "Mechanical impedance of layered tissue," *Medical Progress through Technology*, supplement to vol. 21, pp. 1-4, 1997) is important in applications like needle-free injection (B. D. Hemond, et al., "A Lorentz-force actuated autoloading needle free injector," in 28$^{th}$ *Annual International Conference of the IEEE EMBS*, pp. 679-682, 2006), where the dynamic response of skin to a perturbation is important in determining the required injection depth.

Linear stochastic system identification techniques have been used to describe a variety of biological systems (M. P. Ottensmeyer, et al., 2001; G. Boyer, et al., 2009; M. Garcia-Webb, et al., "A modular instrument for exploring the mechanics of cardiac myocytes," *American J. of Physiology: Heart and Circulatory Physiology*, vol. 293, pp. H866-H874, 2007). However, many systems cannot be fully described by linear dynamic models. Investigators have also used nonlinear relationships to describe the stress strain relationship in skin (F. M. Hendricks, et al., 2003). However, most of this work has been done at low frequencies and therefore does not describe the dynamic properties of skin.

Another problem with existing methods is that the dynamics of the testing device are often not characterized and are assumed to apply perfect forces to the tissue. For example, actuators are assumed to have perfect output impedance such that the dynamics of the system being tested do not affect the dynamics of the actuator. In addition, many existing methods and devices are limited to one test geometry and one perturbation scheme. Once a different geometry or testing direction is used, the measured results are not easily comparable.

Trends in consumer skin care have shown the use of specific molecules and proteins, such as tensin, which are well known to cause collagen growth or increase skin suppleness in hydration and anti-aging products. Although standard testing devices for skin have been proposed, industry specialists have expressed dissatisfaction with existing devices.

SUMMARY OF THE INVENTION

The present invention generally is directed to devices and methods for measuring one or more mechanical properties of tissue, such as the skin of an animal, skin of a fruit or vegetable, plant tissue, or any other biological tissue.

A device for measuring a mechanical property of a tissue includes a probe configured to perturb the tissue with lateral movement relative to a surface of the tissue, an actuator coupled to the probe to move the probe, a detector configured to measure a response of the tissue to the perturbation, and a controller coupled to the actuator and the detector. The controller drives the actuator using a stochastic sequence and determines the mechanical property of the tissue using the measured response received from the detector.

The probe can be placed against the tissue surface and may be coupled to the tissue surface, for example using a static preload or an adhesive. The device can further include a reference surface configured to contact the tissue surface. The probe may include a set of interchangeable heads, the set including a head for lateral movement of the probe and a head for perpendicular movement of the probe.

Lateral movement of the probe is movement directed across the surface of the tissue and may be used to extend the tissue with the probe or to slide the probe across the tissue surface to measure surface mechanics. Interchangeable heads for lateral movement may be configured differently for extension than for surface mechanics testing. Perpendicular movement is movement normal to the surface of the tissue and may be used to indent the tissue, which can include pushing and pulling on the tissue.

In general, the perturbation can include indentation of the tissue with the probe, extension of the tissue with the probe, or sliding the probe across the tissue surface. In some embodiments, the actuator includes a Lorentz force linear actuator and perturbing the tissue can include using the Lorentz force linear actuator.

The mechanical property may be determined using non-linear stochastic system identification. The mechanical properties may be indicative of, for example, tissue compliance and tissue elasticity.

In some embodiments, the detector includes a force sensor detecting force of the perturbation, for example, using a current sensor detecting a current input to the actuator. The detector can include a position sensor detecting displacement of the tissue surface. The device can further include a handle for manual application of the probe to the surface of the tissue and may include an accelerometer detecting an orientation of the probe. Probe types can include indentation, extension and surface mechanics (sliding). Additional attachment methods may include twist-and-pull microhooks or suction.

A method of measuring the mechanical properties of tissue includes placing a probe against a surface of the tissue, mechanically perturbing the tissue with lateral movement of the probe using a stochastic sequence, measuring a response of the tissue to the perturbation, and determining the mechanical properties of the tissue based on the measured response to the perturbation.

Determining the mechanical properties can include using non-linear stochastic system identification and may further include modeling the probe and tissue as a system comprising a linear dynamic component and a non-linear static component. The non-linear component may include a Wiener static nonlinear system and the linear component may include a second order mechanical system. In some embodiments, using non-linear stochastic system identification includes using a Volterra Kernel method. Further, the method may include detecting force of the perturbation with respect to a reference surface. Measuring a response can include detecting displacement of the tissue surface with respect to a reference surface.

A method of testing produce, e.g., fruits and vegetables, includes placing a probe against a skin of a piece of produce, mechanically perturbing the piece of produce with the probe, measuring a response of the piece of produce to the perturbation, and analyzing the measured response using non-linear stochastic system identification.

Perturbing the piece of produce can include using a Lorentz force linear actuator and may include using a stochastic sequence. Analyzing can include determining the mechanical properties of the piece of produce. The mechanical property may be indicative of ripeness.

A method of analyzing the mechanical properties of tissue includes mechanically perturbing the tissue using a stochastic input sequence, measuring a response of the tissue to the perturbation, partitioning the measured response, and generating a representation of the mechanical properties of the tissue based on the partitioned response.

Measuring a response can include detecting position of the tissue. Partitioning can include grouping the measured response into position bins over which the measured response approximates a linear response to the perturbation. Generating a representation can include generating a time-domain representation of the partitioned response. Further, generating a representation can include using orthogonalization of the input sequence based on the position bins and the time-domain representation can include an impulse response for each position bin.

A method of analyzing the mechanical properties of tissue includes mechanically perturbing the tissue with a probe using a stochastic input sequence, measuring a response of the tissue to the perturbation, analyzing the measured response, and, while perturbing, adjusting the input sequence based on the analysis.

Analyzing can include using a non-linear stochastic system identification and may include obtaining a distribution, such as a probability density function, of the measured response. In an embodiment, analyzing includes determining a mechanical property of the tissue. Further, the method may include generating the stochastic input sequence.

The present invention has several advantages. Embodiments of the invention are capable of measuring the mechanical properties of skin in a clinical setting because they are low cost and robust, because they enable the testing procedure to be fast and accurate, and because they can be implemented in a hand-held form factor. In addition, devices and methods disclosed herein are able to fully characterize the dynamic linear and nonlinear aspects of the mechanical behavior of skin.

A benefit of using non-linear stochastic system identification to measure tissue properties is that measurements can be done in vivo. Another benefit is that tests can be conducted quickly and each test can obtain as much information as possible. For example, the devices and methods described herein can be used to characterize the parameters of human skin using nonlinear stochastic system identification, which can be completed within 2 to 4 seconds when perturbing the skin using indentation. As an additional benefit of using non-linear stochastic system identification, the data acquisition and analysis method is relatively immune to the movements of the patient during the test.

Embodiments of the invention can provide quantitative measurements and may be used to standardize the qualitative measurements that physicians currently use to diagnose tissue diseases. A device with the ability to diagnose tissue diseases (e.g. Scleroderma, Myxoedema, or connective tissue diseases) or identify the presence of dehydration can have a large societal impact in healthcare and large market impact in terms of tools that are available to clinicians. Quantitative measurements in a clinical setting can advance the field of tissue mechanics by standardizing assessments made by different individuals. In addition, devices and methods disclosed herein can be used for understanding mechanics for manufacturing artificial prosthetic tissue, for determining mechanical properties in locations that are difficult to palpate (such as in the colon during endoscopy), and determining parameters needed for needle-free injection.

While different types of tests and devices can be used to identify the anisotropic properties of skin, for in vivo testing, the contribution from directions outside the testing plane can affect the results. The disclosed devices methods are capable of testing multiple directions, by using different perturbation modes and interchangeable probe heads, which can be useful in determining these anisotropic material properties.

Furthermore, embodiments of the invention can be used to quickly measure the mechanical properties of plant tissue, such as fruits and vegetables, which can be beneficial for harvesting, processing, and packaging applications in agricultural, commercial, or industrial environments. In addition, a consumer may use an embodiment of the invention, such as a handheld measuring device, to test fruits and vegetables for ripeness, crispness, or freshness prior to purchase.

Another benefit is that embodiments of the invention can provide a standardized measurement technique designed to assess the effectiveness of skin care products. The disclosed method can be used to distinguish the change in skin properties after dehydration or after application of commercial products, such as lotions, creams, and anti-aging products.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 3A is a top view of the hand-held version of a device for measuring tissue properties. The device is configured for extension.

FIG. 3B is a cross-sectional view of the device taken along line C-C of FIG. 3A.

FIGS. 3C and 3D are perspective and front views, respectively, of the device of FIG. 3A.

FIG. 4A is a top view of the hand-held version of a device for measuring tissue properties. The device is configured for surface mechanics testing.

FIG. 4B is a cross-sectional view of the device taken along line D-D of FIG. 4A.

FIGS. 4C and 4D are perspective and front views, respectively, of the device of FIG. 4A.

FIG. 13 shows plots of Volterra kernels for an example of skin measurements using an embodiment of the invention.

FIG. 21 shows results from skin property measurements in a surface mechanics configuration with and without a lotion applied to the skin. FIG. 21 A shows plots of the impulse responses and FIG. 21B shows the fitted parameter data for compliance and damping.

DETAILED DESCRIPTION OF THE INVENTION

A description of example embodiments of the invention follows.

The present invention generally is directed to devices and methods for measuring one or more mechanical properties of tissue, such as the skin of an animal, skin of a fruit or vegetable, plant tissue, or any other biological tissue.

Embodiments of the invention use nonlinear stochastic system identification to measure mechanical properties of tissue. Nonlinear stochastic system identification techniques have been previously used with biological materials, but not to characterize skin tissue. For details of the techniques, see the articles by Hunter and Korenberg 1986 (I. W. Hunter, et al., "The identification of nonlinear biological systems: Wiener and Hammerstein cascade models," *Biological Cybernetics*, vol. 55, pp. 135-144, 1986; M. J. Korenberg, et al., "Two methods for identifying Wiener cascades having non-invertible static nonlinearities," *Annals of Biomedical Engineering*, vol. 27 pp. 793-804, 1999; M. J. Korenberg, et al., "The identification of nonlinear biological systems: LNL cascade models." *Biological Cybernetics*, vol. 55, pp. 125-13, 1986), the entire contents of which are incorporated herein by reference.

The design of the mechanical device preferably includes an easily controllable actuator and force sensing system, a low-cost position sensor, a temperature sensor, an injection-moldable external bearing system and swappable device probes. To minimize the space necessary for the sensor and the cost of the sensor, a linear potentiometer may be used, although other position sensors can be used, including non-contact LVDTs, encoders and laser systems.

Figure 1:
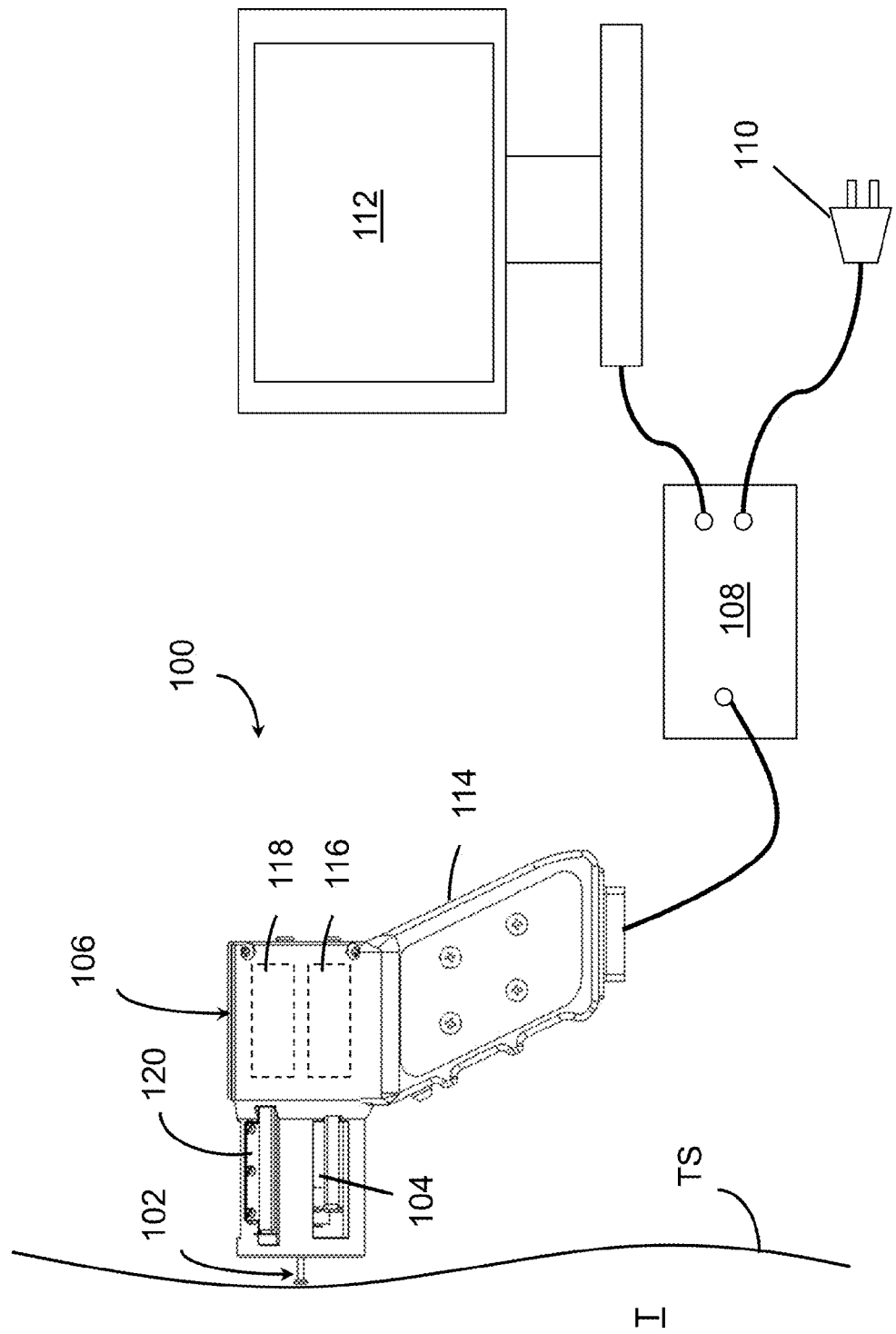
FIG. 1 illustrates a device for measuring tissue properties in accordance with the invention.

FIG. 1 is a schematic view of a device 100 for measuring tissue properties according to the invention. Device 100 includes a probe 102 configured to perturb the tissue T, an actuator 104 coupled to the probe 102 to move the probe, a detector 106 configured to measure a response of the tissue to the perturbation, and a controller 108 coupled to the actuator 104 and the detector 106. The controller drives the actuator 104 using a stochastic sequence and determines the mechanical properties of the tissue using the measured response received from the detector 106. The controller 108 may include or may be connected to a power supply 110. The controller can be a microprocessor or a personal computer and may be connected to or include a display 112, for example, for displaying a user interface. Actuator 104 preferably is a Lorentz for linear actuator or voice coil.

Although the device 100 of FIG. 1 is shown in a configuration for indenting the tissue T with probe 102, device 100 may be reconfigured and used for perturbing the tissue by extending the tissue surface TS with probe 102, or sliding probe 102 across a tissue surface TS. FIG. 1 is shown with the reference surface 39 (see FIG. 2) not in contact with the tissue surface TS. During operation, the reference surfaces and probes are in contact with the tissue surface TS.

Although shown as separate elements in FIG. 1, controller 108, power supply 110, and computer and display 112 may be integrated into an enclosure of device 100, in which case power supply 110 may include a battery. The device 100 can further include a handle 114 for manual application of the probe 102 to the surface of tissue T and may include an accelerometer 116 detecting an orientation of the probe 102. The handle 114 may serve as an enclosure for holding other parts of the device 100, such as controller 108, power supply 110, or accelerometer 116. Accelerometer 116 may be included in or connected to detector 106.

In some embodiments, detector 106 includes or is connected to a force sensor 118 detecting force of the perturbation, for example, using a current sensor detecting a current input to actuator 104. The detector 106 can include a position sensor 120 detecting displacement of the tissue surface TS, for example, using a linear potentiometer, such as potentiometer 31 (FIG. 2A), which detects the position of probe 102.

In use, the device 100 is typically held by an operator at handle 114. The operator places probe 102 against surface TS of tissue T and triggers the mechanical perturbation of tissue T through controller 108 or with a switch, such as trigger 10 (FIG. 2). The controller 108 then drives actuator 104 using a stochastic sequence, which may be an input voltage or current to actuator 104. Actuator 104 moves probe 102, which perturbs tissue T.

As illustrated, device 100 is configured for indentation. The front of the device faces the tissue surface TS. In this configuration, the probe 102 is placed perpendicular to the tissue surface TS and actuator 104 moves probe 102 to indent tissue T (see also FIG. 5A). In other configuration, the top of device 100, which can include a reference surface, such as surface 41 shown in FIGS. 3B and 4B, may be placed against the tissue surface TS. Perturbation then occurs with lateral movement of the probe 102 relative to the tissue surface TS. Lateral movement of the probe can be used for tissue extension, where the probe is coupled to the tissue surface TS, or for surface mechanics testing, where the probe slides across the tissue surface TS (see also FIGS. 5B-C). During or following the perturbation, detector 106 can measure a tissue response, which is received by controller 108 for determining a mechanical property of the tissue based on the measured response. Results of the measurement may be displayed on display 112. The operator may repeat the measurement at the same tissue location, or may move the probe to a different location. Alternatively or in addition, the operator may change the configuration of device 100, for example from indentation to extension measurement, reposition the device on the tissue surface TS according to the new perturbation configuration, and perform another measurement at the same location.

Figure 10B:
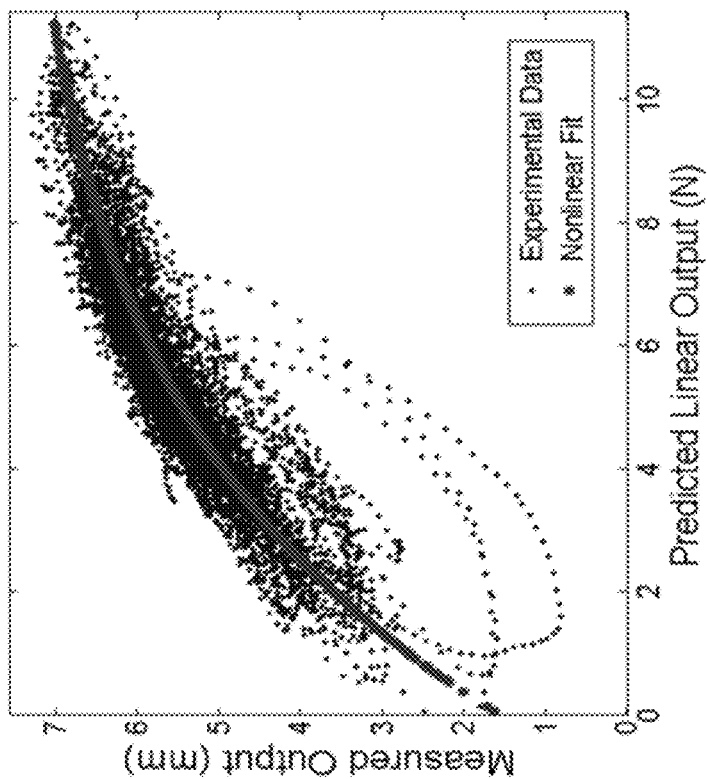
FIG. 10B shows a plot of measured output against predicted linear output illustrating a static nonlinearity.
Figure 10A:
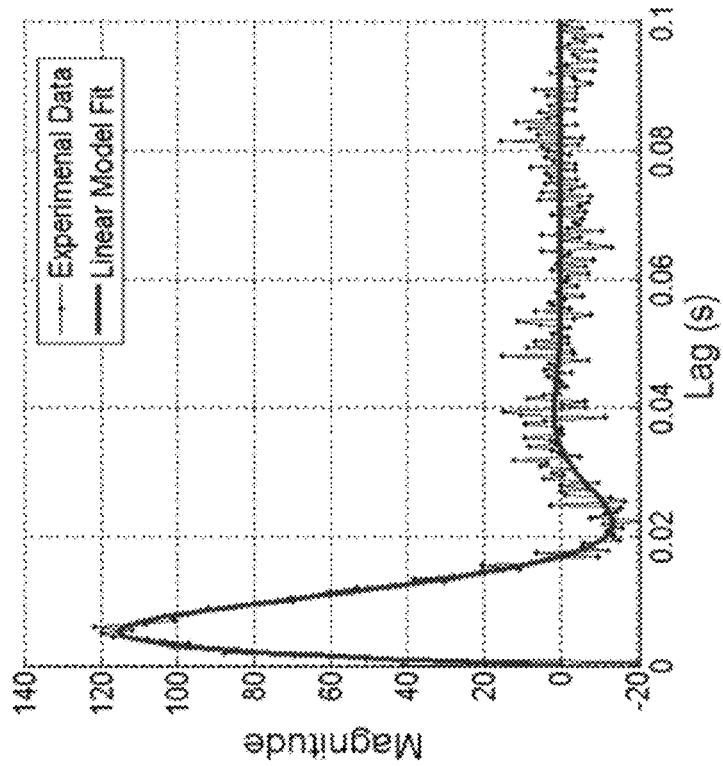
FIG. 10A shows the impulse response with parametric fit of the system shown in FIG. 6.

Determining the mechanical property can be implemented in hardware and software, for example using controller 108. Determining can include using non-linear stochastic system identification and may further include modeling the probe and tissue as a system comprising a linear dynamic component and a non-linear static component, as shown in FIGS. 10A and 10B, respectively. Skin tissue, for example, is a dynamically nonlinear material. As long as the nonlinearity is monotonic, the system can be broken up and analyzed as a linear dynamic component and a nonlinear static component. The non-linear component may include a Wiener static nonlinear system and the linear component may include a second order mechanical system, as described in the article by Y. Chen and I. W. Hunter entitled, "In vivo characterization of skin using a Wiener nonlinear stochastic system identification method, 31st Annual International Conference of the IEEE Engineering in Medicine and Biology Society, pp. 6010-6013, 2009, the entire contents of which are incorporated herein by reference.

In some embodiments, using non-linear stochastic system identification includes using a Volterra Kernel method. Such a method is described in the article "The Identification of Nonlinear Biological Systems: Volterra Kernel Approaches," by Michael J. Korenberg and Ian W. Hunter, *Annals of Biomedical Engineering*, vol. 24, pp. 250-269, 1996, the entire contents of which are incorporated herein by reference. Further, the method may include detecting the force of the perturbation with respect to a reference surface using force sensor 118. Measuring a response can include detecting displacement of the tissue surface with respect to a reference surface.

Tissue T, FIG. 1, may be produce, i.e., fruits and vegetables, and tissue surface TS may be the skin of a piece of produce. In an embodiment, a method of testing produce includes placing probe 102 against skin TS of a piece of produce T, mechanically perturbing the piece of produce with the probe, measuring a response of the piece of produce to the perturbation, and analyzing the measured response using non-linear stochastic system identification. Analyzing can include determining mechanical properties of the piece of produce T. The mechanical property may be indicative of ripeness of the fruit or vegetable T.

In an embodiment, device 100 may be used to implement a method of analyzing mechanical properties of tissue T that includes an output partitioning technique to analyze the nonlinear properties of biological tissue. The method includes mechanically perturbing the tissue T with probe 102 using a stochastic input sequence and measuring a response of the tissue T to the perturbation, for example using detector 106 to detect position of tissue T. Controller 108 partitions the measured response and generates a representation of the mechanical properties of the tissue based on the partitioned response. Partitioning can include grouping the measured response into position bins over which the measured response approximates a linear response to the perturbation. Generating a representation can include generating a time-domain representation of the partitioned response, which may include a kernel or an "impulse" response for each position bin. Further, generating a representation can includes using orthogonalization of the input sequence based on the position bins. Additional details of the partitioning technique are described with reference to FIG. 15.

In an embodiment, device 100 shown in FIG. 1 may be used to implement a method of analyzing mechanical properties of tissue using real-time system identification, such as described elsewhere herein. The method can include mechanically perturbing the tissue T with probe 102 using a stochastic input sequence, which may be generated in real time, measuring a response of the tissue to the perturbation, for example using detector 106, analyzing the measured response, and adjusting the input sequence based on the analysis while perturbing the tissue. Analyzing and adjusting, which can include adjusting the input sequence in real time, may be implemented in controller 108. In analyzing the measured response, the controller 108 may implement algorithms for obtaining a distribution of the measured response and for performing non-linear stochastic system identification.

FIGS. 2A-4D show a hand-held version of an embodiment of device 100 for measuring tissue properties. FIGS. 2A-2D show device 100 in an indentation configuration, FIGS. 3A-3D in an extension configuration, and FIGS. 4A-4D in a surface mechanics testing configuration.

Figure 2A:
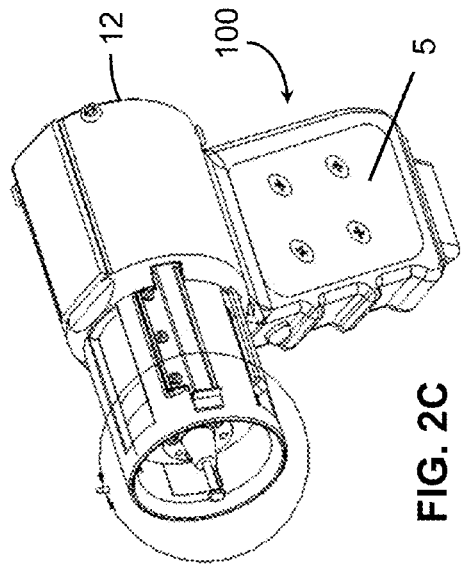
FIG. 2A is a top view of a hand-held version of a device for measuring tissue properties in accordance with the invention. The device is configured for indentation.

As shown in FIG. 2A, device 100 includes probe 102, actuator 104 coupled to the probe 102 to move the probe, detector 106 configured to measure a response of the tissue to the perturbation, and handle 114.

Figure 2B:
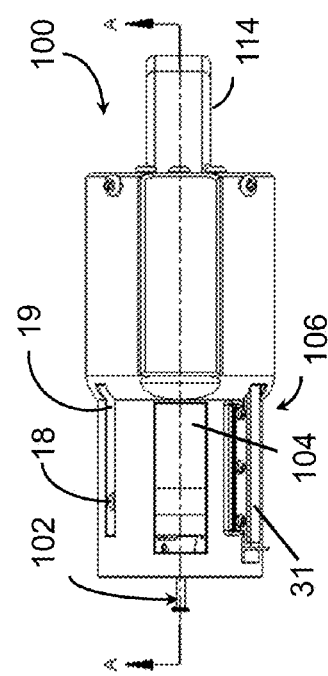
FIG. 2B is a cross-sectional view of the device taken along line A-A of FIG. 2A.
Figure 2C:
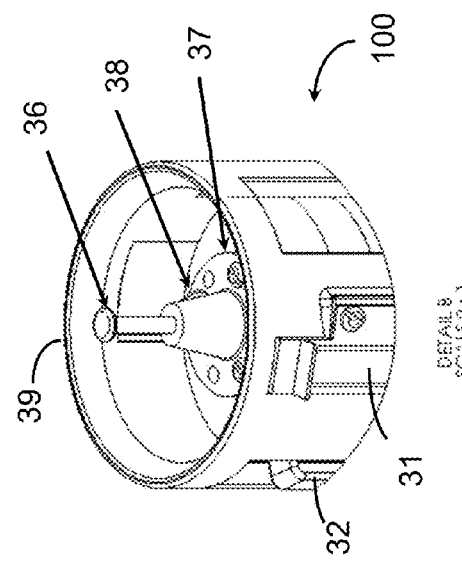
FIG. 2C is a perspective view of the device of FIG. 2A.

FIG. 2B is a cross-sectional view of device 100 taken along line A-A of FIG. 2A. Handle 114 includes handle base 4 that houses trigger button 10 and internal wires 33, which connect trigger button 10 to connector plug 11. Connector plug 11 can provide for electrical connections to an external controller 108, computer 112, and power supply 110 (FIG. 1). A handle cover 5 (FIG. 2C) can be attached to handle base 4. Handle cover 5 can be supported by handle cover mounting standoffs 6 and secured in place by, for example, screws inserted in mounting holes 7. Handle base 4 can be attached to applicator body 12 via a sliding attachment 8 and secured via mounting holes 9 and screws.

Applicator body 12 provides an enclosure which fixtures the actuator 104, the position sensor 106, one or more position reference surfaces, e.g., reference surface 39 (FIG. 2D), and internal wiring guides, e.g., for electrical wires 32 and 33. The body 12 of the device doubles as an encasement for a magnet structure 21 and as a bearing surface for a bobbin 23. Teflon bearing spray may be used to reduce static friction and help create constant dynamic damping. The applicator body 12 may be injection-molded and made from plastic. Screws 17 are positioned in back plate 14 of applicator body 12. The applicator body 12 includes a slot 19 (FIG. 2A) in which a pin 18 is positioned.

As shown in FIG. 2B, actuator 104 is a Lorentz force linear actuator or voice coil—that includes an iron core 20 to guide the magnetic field, magnet 21, steel plate 22, bobbin 23, and coil 26, which may be made from copper.

Lorentz Force Linear Actuator

The Lorentz force is a force on a point charge caused by an electromagnetic field. The force on the particle is proportional to the field strength $B_e$ and the current I* that is perpendicular to the field multiplied by the number $N_e$ of conductors of a coil in series each with length $L_e$. When a current is applied to the coil 26, the charges interact with the magnetic field from the permanent magnet 21 and are accelerated with a force. An actuator which is designed to apply a force directly (rather than through force feedback) is desirable for high-bandwidth operation. In addition to speed, a Lorentz force actuator allows for a large stroke in order to test the depth dependent nonlinearities in skin, for example when using an indentation probe.

The power handling capabilities of a coil are limited by its heat generation (due to ohmic heating) and its heat dissipation capabilities. The housing for many coils provides heat sinking abilities preventing the coil from heating too quickly. In addition, a moving coil can provide convective cooling. The most commonly used forces and test lengths for this device would not require advanced heat handling measures but a temperature sensor 28 can be added as a safety measure to monitor the temperature for high force or extended length tests.

In addition to the relatively simple operating principles, the Lorentz force linear actuators where chosen for the following reasons.

Direct force control: The Lorentz force coil can be driven to produce a force as commanded since current is proportional to force and voltage is proportional to velocity. Forces less than 15 N would require that the actuator used in tissue testing be driven at voltages lower than 48 V. Directly controlling force open loop gives advantages for proving the identifiability of system parameters when compared to servo-controlled stages.

Incorporated force sensing: The force can be measured by looking at the current flowing through the actuator. This can be the most low-cost method for measuring force. For some separate force sensors, there are additional dynamics, which are detrimental to the system identification process.

High force limits: The coil can be driven to high forces which may be limited by the amplifier and the heat transfer properties of the actuator.

Long stroke: The coil can be designed with a long stroke with relatively large regions of linear operation. Other systems like those driven by piezo-electrics do not have as high a stroke and do not generally operate at low voltages.

High bandwidth: The bandwidth of a Lorentz force coil is limited by input power, the mass of the system, and the stiffness of the tissue being tested. Other actuation strategies, such as lead screw systems, have relatively low bandwidth in comparison.

Low cost: The actuator consists of a magnet, a steel cap, an iron core to guide the magnetic fields, and a copper coil. The simplicity of the design helps reduce cost.

Few accessories necessary: In order to operate the coil, the only accessories outside the actuator can be an amplifier and power system. Other perturbation strategies, such as non-contact pressure systems, require an additional high pressure pump and valves.

Device Construction

In accordance with an embodiment of the invention, several implementations of devices were constructed, including a desktop device and a hand-held device, such as device 100 shown in FIGS. 2A-4D. To minimize the space necessary for the position sensor and the cost of the sensor, a linear potentiometer can be used.

According to an embodiment of the invention, a desktop version (not shown) of device 100 includes a Lorentz force linear actuator, such as actuator 104, with a bobbin mass of 60 g, a total length of 32 mm, and an inner diameter of 25.2 mm. To construct the actuator, a magnet structure (BEI Kimco Magnetics) was used with a neodymium magnet with a magnetic field strength of 0.53 T. A custom designed overhung bobbin, such as bobbin 23, was 3D printed with multiple attachments for a temperature sensor, such as sensor 28, easily insertable electrical connections, through holes, such as holes 35, to allow air flow, threaded holes, such holes 34, for attachment of custom probe tips or heads, and a wire insertion slot. In one embodiment, the custom wound coil has a resistance of 12Ω, inductance of 1.00 mH, and 6 layers of windings using 28 gage wire.

Embodiments of device 100, in both the desktop and handheld version, include a force sensing system via a current sense resistor. The coil design also includes the integration of a small temperature sensor 28, such as OMEGA F2020-100-B Flat Profile Thin Film Platinum RTD, into the side of the coil 26. This RTD monitors the temperature of coil 26 to prevent actuator burn-out. A low-cost linear potentiometer 29, such as ALPS RDC10320RB, can be used to measure position. When implemented with an amplifier and 16-bit DAQ the position resolution is as low as 0.5 μm.

In the desktop version of device 100, attachment 8 allows applicator body 12 to be slid into modular aluminum framing (MK automation) instead of a custom handle, such as handle 114 of the handheld version of the device shown in FIG. 2. For indentation, the desktop version of the device can utilize gravity to provide an extra constant preload on the surface of the tissue.

The framing attached to a base allows the testing system to have a small and stiff structural loop that enables device 100 to be more precise and helps eliminate system noise. The more important structural loop, however, is the one between the rim of the actuator, such as reference surface 39, and the system or tissue being tested. This is because forces and positions are being measured with respect to the reference surface, thereby allowing device 100 to characterize tissue compliance.

The handheld system is typically smaller than the desktop system and therefore has a lower force output. A handheld version of device 100 was constructed according to an embodiment of the invention. In one embodiment, the stroke of the actuation system of the handheld device is nominally 32 mm, the bobbin resistance is 9.5Ω, and the magnetic field strength is 0.35 T. In addition, the mass of the actuator, for example, is 39.5 g and the total mass of the handheld device, for example, is 256 g.

As long as the reference surface, such as reference surface 39 or 41, is placed in firm contact with the surface of the patient's skin, the system will successfully measure the compliance transfer function of the skin and not of other components. To account for force changes when going from measurements in the desktop system with respect to the handheld system, two additional components can be added. A bracing band may be used to help maintain the lateral position of the actuator on the skin. An accelerometer may also be added to account for the orientation of the handheld version of device 100 and to compensate for the directional loading differences from gravity.

Device Configurations

Figures 5A, 5B, 5C:
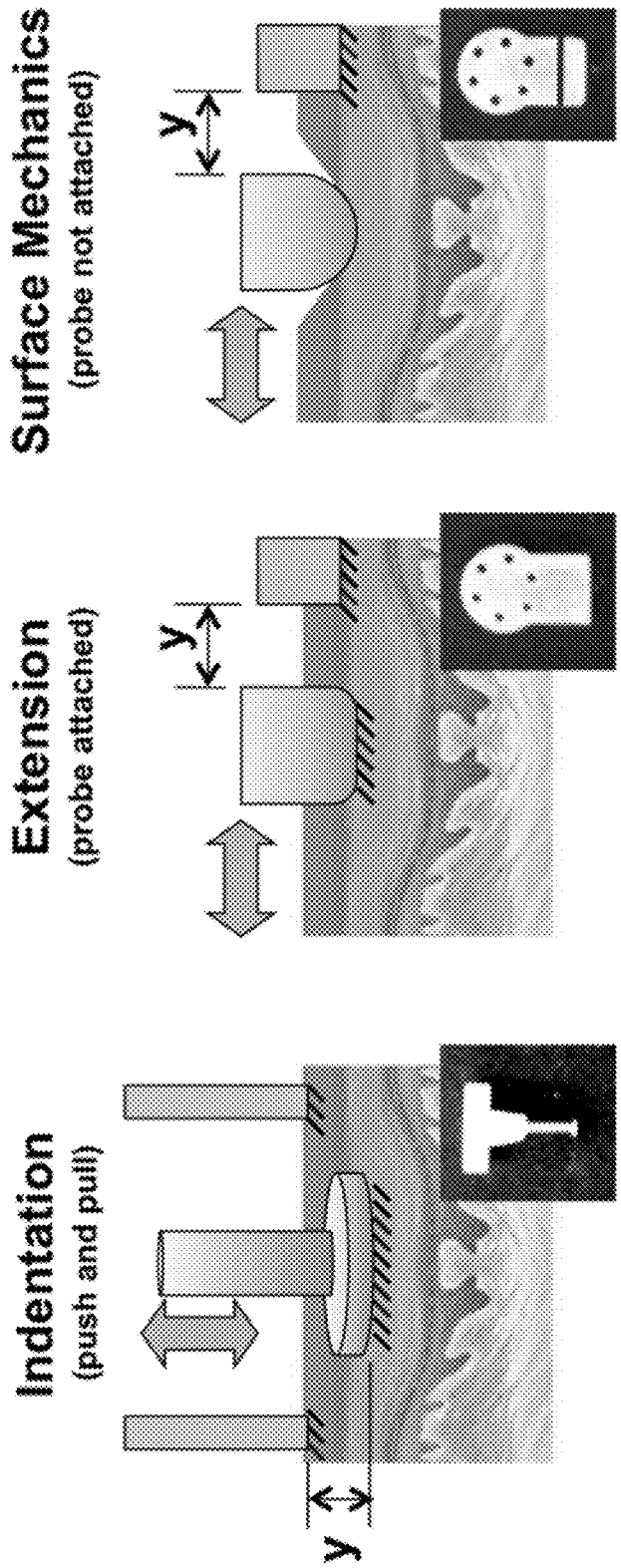
FIGS. 5A, 5B and 5C illustrate different configurations of a device for different modes of perturbation, including an indentation configuration, extension configuration, and surface mechanics configuration.

The design of the instrument allows for several different in vivo system identification modes including probe indentation, extension, and surface mechanics testing depending on the custom probe type used. FIGS. 5A-5C illustrate the different configurations for device 100. Small insets show examples of probe heads suitable for each test configuration.

Figure 2D:
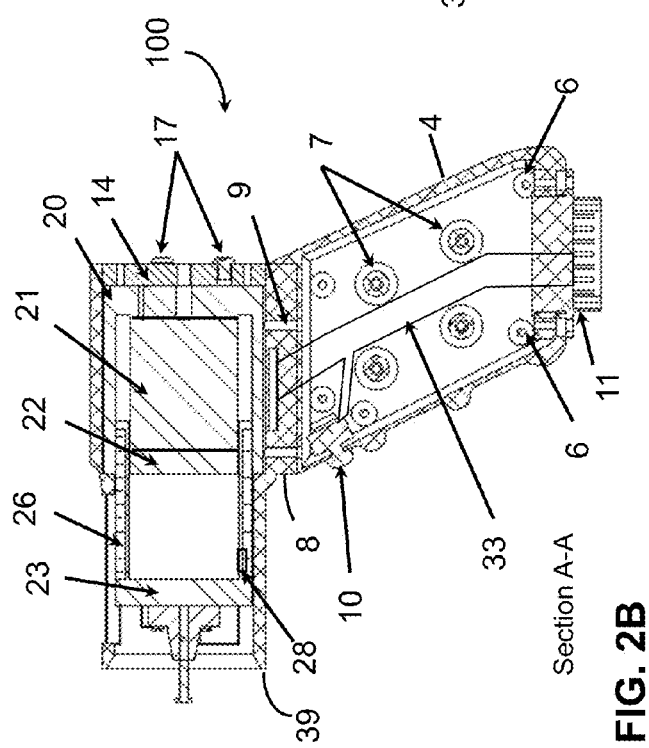
FIG. 2D is a detail view of detail B of FIG. 2C.

For indentation, FIG. 5A, a typical tip used for contacting the skin is a 4.4 mm steel disk with a normal thickness of 1 mm. For example, a smaller probe tip having a 4.3 mm diameter and 0.4 mm corner radius or a larger probe tip having a 5 mm diameter and 1.3 mm corner radius may also be used. FIG. 2D shows indentation head 38 including tip 36 mounted to bobbin 23 of device 100 via probe mount 37. Tips with different thickness, diameters, and corner radii can also be used. The attachment to bobbin 23 of the actuator is recessed to allow the skin to freely conform without contacting other parts of the probe. All indentation measurements, such as position or displacement of the tissue, are made with respect to the position reference surface 39 that is significantly larger than the circle of influence from probe tip 36. The measurement of position of the probe tip relative to the reference surface is indicated by the arrow labeled y in FIG. 5. For indentation into the skin, e.g., pushing normal to the skin surface, no taping or gluing is necessary. However, to do experiments that require lifting or pulling the skin, the probe must be coupled to the skin surface using, for example, suction, liquid bandage, or some other type of mild glue.

For extension experiments, FIG. 5B, the probe moves laterally, as indicated by arrow y, relative to the tissue surface and another probe head and reference surface are used. FIG. 3A-3D show a handheld device 100 configured for extension testing. In one embodiment, the extension probe head 40 is 5 mm by 16 mm with rounded edges that have a 2 mm radius. The rounded edges, also shown in FIG. 5B, are important for reducing stress concentrations. The reference surface 41 can be a flat face on the body 12 of device 100. It serves as the second probe surface and measurements of skin displacement are made relative to the reference surface 41. This is illustrated in FIG. 5B by arrow y. Coupling to the skin can be provided by a normal, i.e., perpendicular, preload and a mild layer of liquid bandage or double-sided tape. The extension system can be oriented along the Langer's lines or in other orientations to characterize anisotropic tissue properties.

Surface mechanics testing, FIG. 5C, or friction assessment, is configured in a manner similar to extension experiments except that the probe is more rounded and allowed to slide along the surface of the skin. Since the surface mechanics system is second order with a pole at the origin, an external spring is needed in the system to complete linear stochastic system identification. FIG. 4A-4D show a handheld device 100 configured for extension testing. Surface mechanics probe or head 42 includes probe tip 43 and spring 45. Also included may be linear guides 46 and force sensor 44. The measured compliance will be a function of the depth of the compression of the probe into the skin depending on the vertical preload.

System Model

Figure 6:
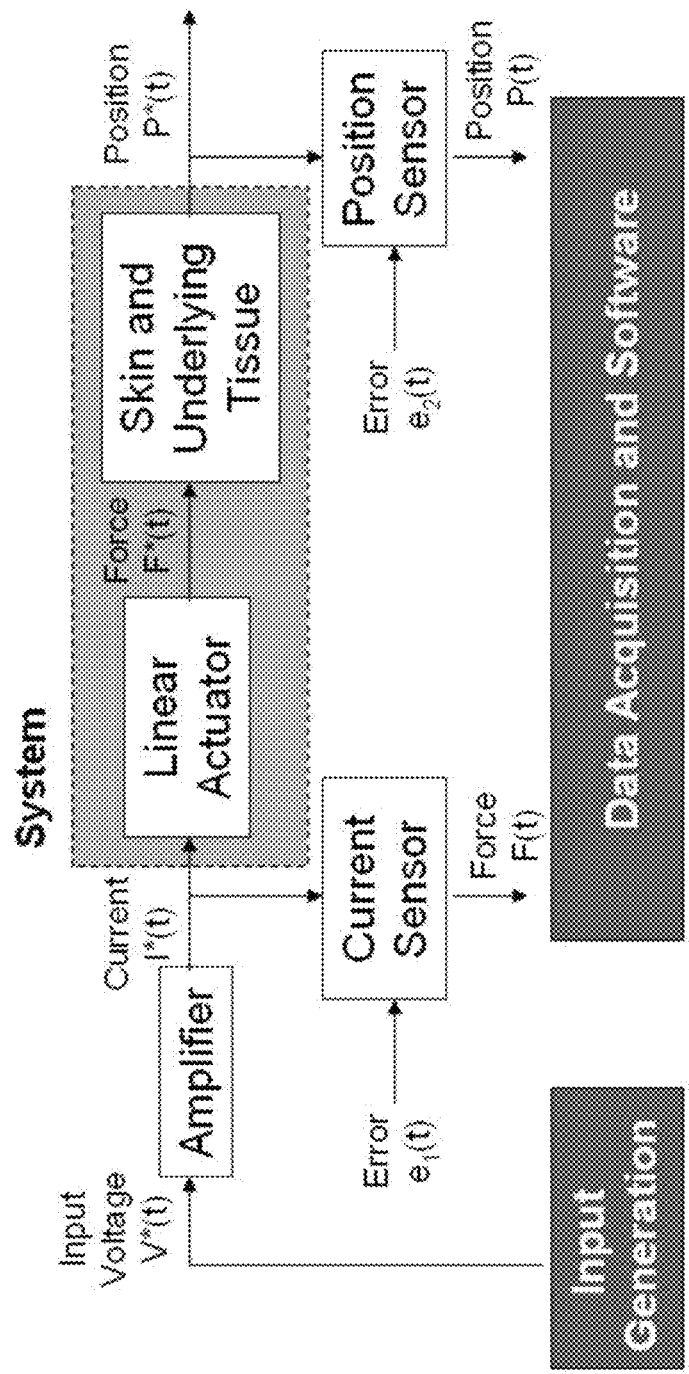
FIG. 6 is a schematic diagram of a system for measuring tissue properties according to the invention.

FIG. 6 shows the schematic diagram of a system for measuring mechanical properties of tissue, e.g., skin tissue, along with inputs and outputs. The system includes the actuator and tissue dynamics and is based on the use of a Lorentz force linear actuator. The actuator, such as actuator 104, has an inherent mass and the bearings and air resistance have inherent damping. There are two possible methods for treating the nonparametric or parametric information that can be derived from the identification of this system. Either the system can be treated as a whole (e.g. the derived mass is a system mass) or the system can be treated as a linear addition of actuator parameters and tissue parameters (e.g., the derived mass is composed of the actuator mass acquired from calibration plus the tissue mass). The results given herein are values of the system, which includes both the actuator and tissue, because the actuator, such as actuator 104, cannot be considered to have an isolated input impedance.

In FIG. 6, the input is a voltage $V^*(t)$ sent through a linear amplifier, such as a Kepco BOP 50-8D amplifier, into the force actuator that perturbs the skin. The applied force is $F^*(t)$ and the position is $P^*(t)$. Because of different sources of sensor error $e_1(t)$ and $e_2(t)$, the measured force $F(t)$ is based on the current $I^*(t)$ and the measured position is $P(t)$. The sensors include a current sensor that measures the force output $F(t)$ of the Lorentz force actuator (since current and force are linearly related) and a linear potentiometer to measure the position $P(t)$ of the probe tip. Note that the input generation component is separate from the data acquisition software. Therefore, this system operates open loop. Closed loop input generation can be implemented when the loop is closed between data collection and input generation, as described herein with reference to FIG. 16. Data acquisition may be controlled by a NATIONAL INSTRUMENTS USB 6215 device. A data acquisition software environment, such as LABVIEW 8.5, can be used to implement the control program and user interface.

The force measurement is typically taken after the amplifier, FIG. 6, for several reasons. First, measuring the current after the amplifier skips the amplifier dynamics and any output timing lags of the software. No matter if the input is a voltage or current command, measuring the dynamics after the amplifier is desirable. Second, a force to displacement measurement would create a causal impulse response of the mechanical compliance, which can be analyzed with simpler system identification techniques. Lastly, because the input to the system is directly related to the force output, as opposed to a position-based actuator system, an internal feedback algorithm is not needed. This creates a mathematically simpler system identification situation with the capability to act at higher frequencies; a system with feedback is typically required to operate at a significantly lower frequency than its controller/observer poles and zeros. Because of the configuration of the system, a real-time controller is not necessary for operation but can still be implemented for real-time input generation schemes.

Linear and Static Nonlinear Techniques

Skin tissue is a dynamically nonlinear material. As long as the nonlinearity is monotonic, a system as shown in FIG. 6 can be broken up and analyzed as a linear dynamic component and a nonlinear static component using relatively simple cascade techniques. The linear dynamic component and the static nonlinear component of tissue can be identified using white, Gaussian inputs or non-white, non-Gaussian inputs. In order to identify the static nonlinearity, the predicted linear output is first calculated from the convolution of the nonparametric impulse response and the input. A free constant can be moved between the dynamic linear and static nonlinear estimates. The dynamic linear component can be normalized by dividing the impulse response by the DC compliance. Lastly, the linear and nonlinear identification algorithms may be iterated to create a better overall estimate. Details of the technique are described in the article by Y. Chen and I. W. Hunter entitled, "In vivo characterization of skin using a Wiener nonlinear stochastic system identification method, 31st Annual International Conference of the IEEE Engineering in Medicine and Biology Society, pp. 6010-6013, 2009; and in the article by I. W. Hunter and M. J. Korenberg, 1986.

The exemplary results presented in FIGS. 7-10 were obtained from skin tissue in vivo with the desktop version of device 100 using an indentation configuration as, for example, shown in FIG. 5A. The experimental procedure for obtaining data involves first checking the area of the skin for markings or signs of wear. The tip of the device is then lowered to the skin surface with a predefined preload for 0.5 seconds. The value of the preload is equivalent to the average of the force that is later applied during the test. The system identification input is tailored such that the coil is always in contact with the skin and that the maximum force is less than 10 N to 12 N. Results were obtained from an area of the posterior forearm 40 mm distal from the wrist.

A perturbation input with an appropriate cutoff frequency is first determined followed by linear and nonlinear system identification. Then a parametric model is fitted to the data and the repeatability of the results can be assessed, as described below.

Input Filtering

Stochastic inputs can have a variety of distributions and colors. Examples are Gaussian white inputs or Brownian process inputs, which are the workhorses of classical system identification methods. When a Gaussian distribution is put into a linear system, the output is a Gaussian distribution. When other distributions are put into a linear system, the output distributions will change and will often approach a Gaussian. For nonlinear systems, however, an input Gaussian may turn into another distribution, as shown in FIG. 7 for an exemplary input force and output position distribution of skin under indentation.

The stochastic sequence used to perturb the tissue can be tailored to a range of input frequencies. An input sequence characterized by input cutoff frequency of approximately 200 Hz, implemented with an 8th order Butterworth filter, can give an optimal balance between displacement range, dynamic bandwidth and the noise floor. In one example of measurements, a sampling frequency of 2 kHz was used with a test length of 4 seconds. As little as 2 seconds may be needed to obtain sufficient data for system identification.

Figure 8:
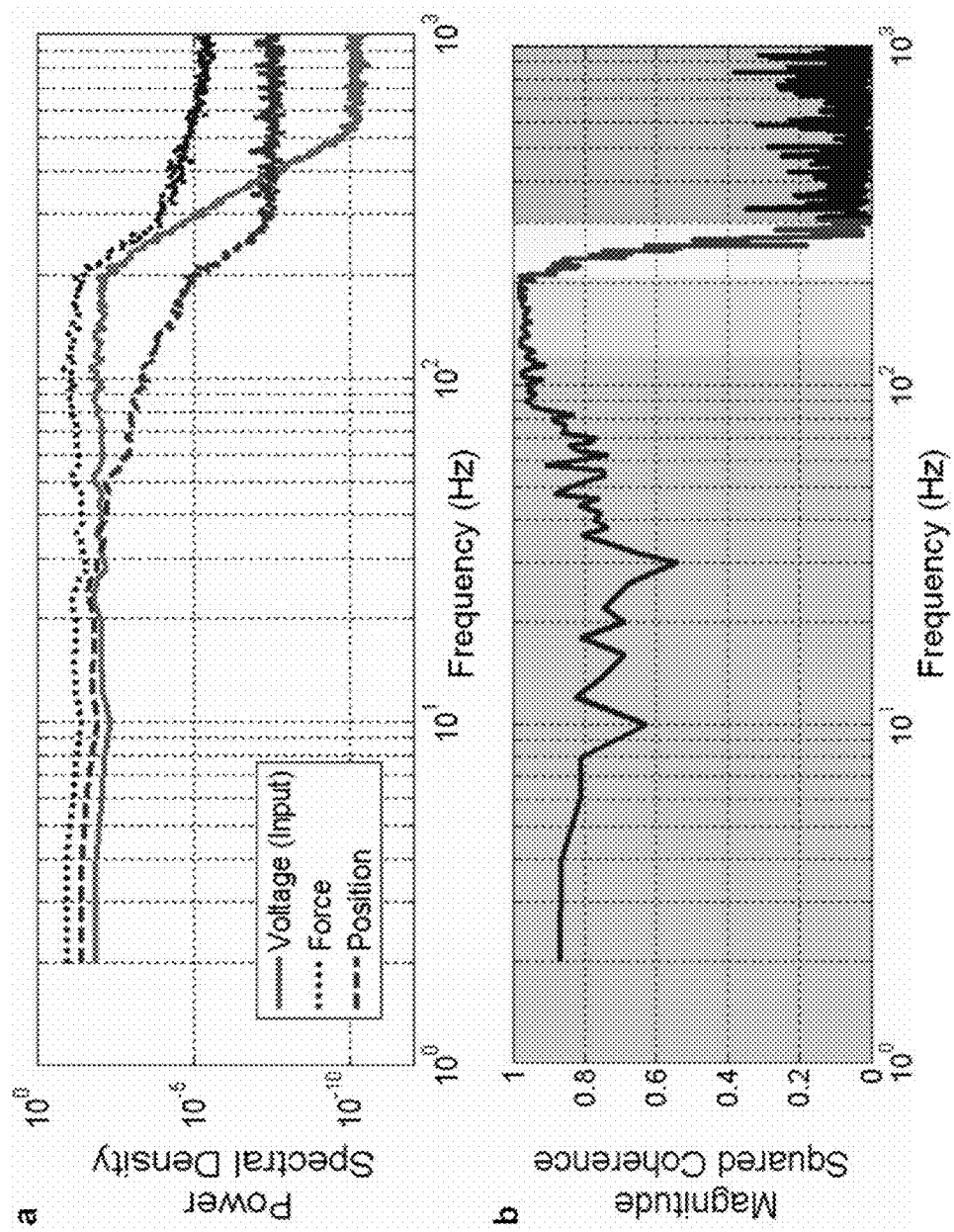
FIG. 8A shows a graph of the power spectral density of the input voltage, the measured force, and the measured position of the instrument during a nonlinear stochastic measurement of the skin during indentation on the left posterior forearm 40 mm from the wrist.
FIG. 8B shows a graph of the mean squared coherence (MSC) of the input force to output position illustrating the frequency ranges that can be explained by linear elements for MSC near unity.

FIG. 8 shows the resulting power spectral density of the input voltage, the measured force and the measured position as well as the coherence squared between the force and the position output of the system in the example. At lower frequencies the system exhibits behavior that may not be explained with a simple linear model since the coherence is less than 1.0.

Linear System Identification

Figure 9:
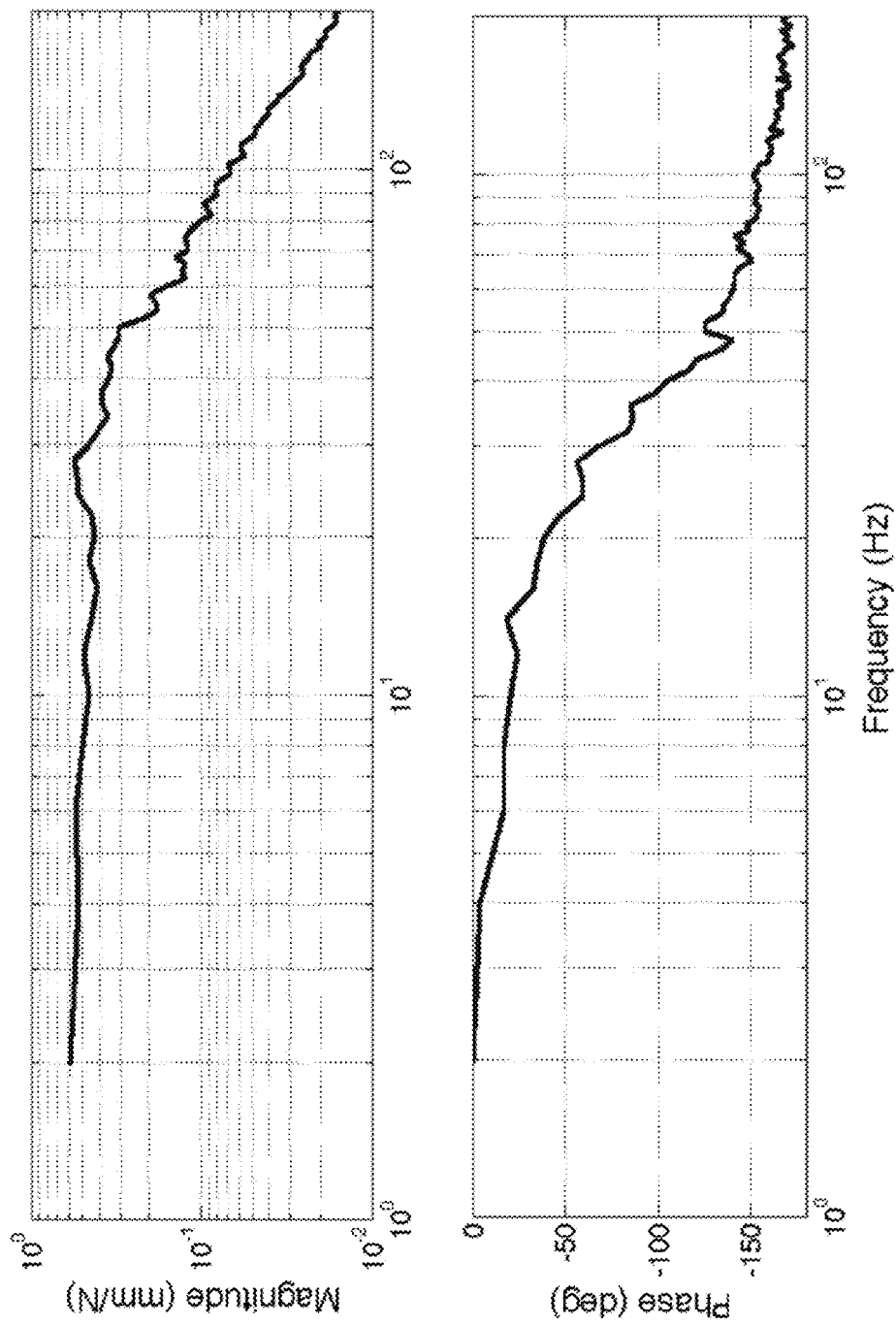
FIG. 9 shows a Bode plot for the force-to-position relationship for skin. The top panel shows the magnitude relationship and the bottom panel the phase relationship. The cutoff frequency is near 40 Hz for this configuration of input mass and skin compliance.

FIG. 9, which shows the Bode plot of the system, can be calculated from the ratio of the cross-power spectrum to the input power spectrum. The cutoff frequency appears near 40 Hz for this configuration of input mass and skin compliance. The impulse response of the system is determined using the method outlined above and as described in the articles by Chen and Hunter 2009, and Hunter and Korenberg 1986. FIG. 10A shows the impulse response of the system. It can be deduced from the impulse response and from the Bode plot that the system has a second order transfer function. A parametric model can therefore be created to obtain intuition about the system.

In this mechanical system, FIG. 6, there is an effective mass $M_e$ (contributions from coil mass and effective inertia of the skin), effective damping $B_e$ (contributions from friction, eddy current damping, skin damping) and effective spring constant $K_e$ (contributions from average skin stiffness). This produces a second order transfer function in the Laplace domain of the form shown in Equation 1 when the input is current driven.

$$\frac{P(s)}{F(s)} = \frac{1}{M_e s^2 + B_e s + K_e}, \quad (1)$$

The impulse response of the second order transfer function can be fitted to the measured data. Before dividing by the DC compliance, the effective mass in one example was found to be 0.0912 kg (the measured probe and bobbin mass was 0.060 kg), the effective damping was found to be 22.77 Ns/m, and the effective spring constant was found to be 4.67 kN/m. The impulse response can then be convolved with the input to create a predicted linear output. The variance accounted for (VAF) of the nonparametric model in the example is 75.79%. The VAF of the second order transfer function (parametric model) is 75.64%.

Wiener Nonlinearity

The predicted linear output can be plotted against the measured output to show a static nonlinearity as is shown in FIG. 10B. The measured output, or the depth into the skin in millimeters (mm), is shown mapped against the predicted linear output in newtons (N). The position shown on the y-axis is the absolute position on the actuator. This is used so that the nonlinearity can be mapped against possible nonlinearities in the actuator to show that the actuator nonlinearities are negligible. The surface of the skin is located at 10 mm on the actuator for this test. Positive values of the predicted linear output indicate forces pressing into the skin and negative values indicate pulling off of the skin. An additional contribution of 0.59 N was added during calibration to account for the contribution of gravity.

After subtracting out the baselines of the data in FIG. 10B, a fit can be obtained of the nonlinearity in the form shown in Equation 2, where z is the predicted linear output (after several iterations) in newtons and g(z) is the nonlinear function in mm to fit y, the measured output. The reason for the change in units is because the nonlinear function was chosen to carry the significant units when the linear dynamics are scaled by a set constant. In this form, the change in stiffness as a function of depth can be represented completely by g(z).

$$y = g(z) = C_1(1 - e^{C_2 z}). \quad (2)$$

In this function, the parameter C1 is a measure of the total compressible thickness of the skin and underlying tissue while C2 can be interpreted as the constant that determines the stiffness of the material at different depths.

Figure 11:
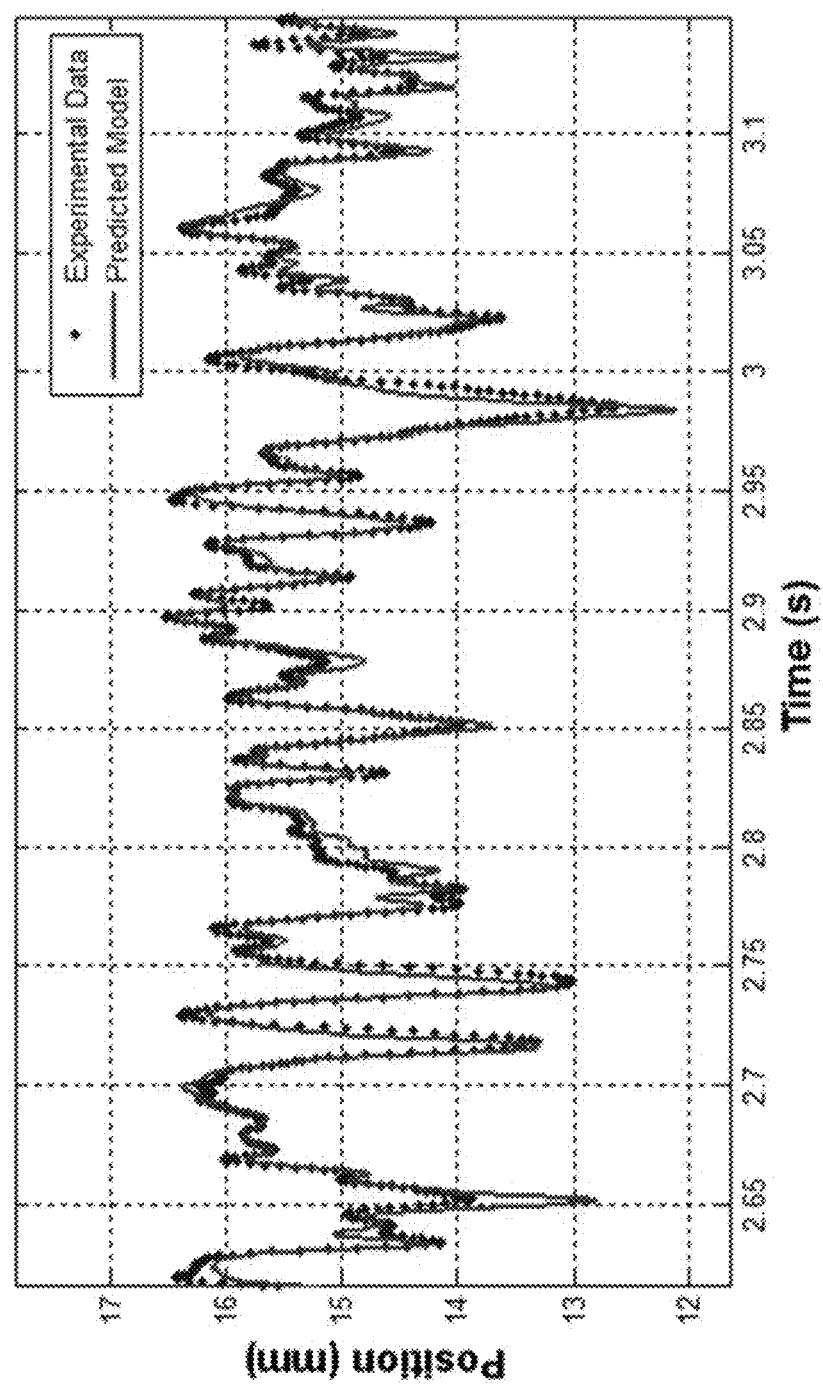
FIG. 11 shows a plot of measured position and predicted position using a Wiener static nonlinearity for measuring tissue properties.

When the nonlinear model is convolved with the original input of the example measurements, a predicted non-linear output can be obtained as shown in FIG. 11. The resulting VAF is 80.7%, an increase of about 5% over the linear model prediction, indicating that the system for measuring tissue properties, such as those of skin, can be better explained by the nonlinear model.

Volterra Kernel Techniques

Instead of using iterative techniques to identify static nonlinearities in an actuator and tissue system, such as Wiener nonlinearities described above, a comprehensive technique for determining the Volterra kernels can be use. The Volterra series is a functional expansion of the general time-invariant nonlinear dynamic system problem. The idea behind the functional expansion is that the zeroth order kernel represents the system average. The first order kernel represents the first order linear perturbation to the system where the output depends linearly on lagged inputs. This kernel is exactly the linear impulse response function. The second order kernel represents the second order perturbation to the system where the "impulse response" function is not a function of one lag but a function of two lags. This means that the input at some time can interact with the input at another time to produce an effect on the output. This concept can be expanded to higher orders. For a system with a finite memory length I, the discrete functional expansion can be written, $$y_s(n) = \\ h_0 + \sum_{i=1}^{I_1+1} h_1(i)x(n-i) + \sum_{i_1=1}^{I_2+1}\sum_{i_2=1}^{I_3+1} h_2(i_1, i_2)x(n-i_1)x(n-i_2) + \ldots + e(n) \quad (3)$$

Equation 3 allows for memory lengths $I_1$, $I_2$, $I_3$, etc., to be different for different kernels. Memory lengths $I_1$, $I_2$, $I_3$, etc., can be the same and may be equal to memory length I. As it stands, the Volterra expansion is difficult to solve; one of the reasons is that the expansion contains many parameters in $h_1$, $h_2$, etc. which grow very quickly with the memory length and kernel order. Secondly, the system is not orthogonal so changing one value will change the optimal fit for other values in the series.

The Volterra kernel is, however, only one functional expansion among many for nonlinear dynamic systems. A modification to the Volterra kernel developed by Norbert Wiener attempts to make solving the system much simpler. The Wiener functional expansion orthogonalizes the Volterra series for an assumed form on the input. By using assumptions for Gaussian white inputs, Wiener was able to create a different expansion such that the first kernel can be solved independent of the second kernel. This means that any noise remaining after solving the first order kernel must either be noise or components of higher order kernels. It is important to note that the Wiener and Volterra kernel solutions are not exactly the same. The zeroth order Wiener kernels are the mean output for one type of Gaussian white input. The first and second kernels, however are the same for the two systems as long as there are no higher order kernels.

Several Wiener kernel solution techniques exist including cross-correlation methods, repeated Toeplitz matrix inversion techniques, and use of functional expansions. The drawback of the Wiener functional expansion is that only white inputs can be used. Since real inputs can only become white asymptotically, there is inherent uncertainty in the solutions for short test lengths. In addition, the input to a real system is rarely optimally Gaussian and white. It is possible to create orthogonal expansions for different types of inputs but not every mathematical function has properties that would allow this to be readily accomplished. In addition, it becomes cumbersome to do system identification if a new expansion needs to be derived for every new input.

There are several different methods that can be used to solve Volterra kernels. The method developed by M. J. Korenberg and I. W. Hunter, "The identification of nonlinear biological systems: Volterra kernel approaches, "*Annals of Biomedical Engineering*, vol. 24, pp. 250-268, 1996, can be generalized to any input. It imposes no constraint on the input type (input does not need to be Gaussian and white to be solved), length, or smoothing constraints used on the kernels. Because of the benefits of the Korenberg and Hunter method, it is used as the basis for techniques described herein for obtaining results, for example, for skin under indentation. Because this method requires a few modifications for the input types used in this work, additional implications and methods for obtaining interpretable kernel data are described.

Exact Orthonormalization Solver

The method by Korenberg and Hunter requires an exact orthonormalization step for the input, a solution step in the orthonormalized space, and a reconstruction step to take the solution back into the space of the Volterra kernel. A summary of the solution steps are shown below and illustrated in FIG. 12:

1. Construct: Sort the input data according to a set of rules.
2. Orthonormalization: Use a modified Gram-Schmidt solver to orthonormalize the input data.
3. Solve: obtain an orthonormalized solution.
4. Resolve: use the inverse of the Gram-Schmidt process to put the solution back into its original terms.
5. Reconstruct: use the same partitioning rules to resolve the kernel responses.

Steps 2 through 4 for the orthonormalization technique are well known. In fact, Gram-Schmit orthogonalization is the exact step used by Wiener to orthogonalize the Wiener kernels. Steps 1 and 5 are dependent on different partitioning rules, which need to satisfy constraints from the modified Gram-Schmidt orthonormalization process. The terms orthonormalization and orthogonalization are used interchangeably here.

A modified version of the technique used by Korenberg and Hunter was developed. This process can be optimized for computational speed in, for example, the MATLAB technical computing environment, and also for numerical stability.

Many physically realizable, finite memory systems can be modeled from an input output relation that is shown, $$y(n) = \sum_{m=1}^{M} A_m P_m(n) + e(n). \quad (4)$$

In the simplest linear case, y(n) is the output of the single input single output system, $A_m$ is the impulse response of the system with memory M and $P_m(n)$ (which is not position in this case) is simply equal to the input x(n−m−1). The measurement contains some error e(n). From this form, one can easily obtain a linear input output relation. In the more general case, m is a value, which stores the dynamic memory of the system, which stores input lag information while n represents the value at a given time. The $P_m(n)$, however stores information for a particular set of rules that apply at a given m and n. This implies that $A_m$ is a series that is convolved with $P_m(n)$ to produce the desired output where $P_m(n)$ is constructed based on some partitioning rule. It is typically difficult to directly solve this equation and therefore needs to be orthonormalized into a different form in terms of variables $\gamma_m$ and $\beta_m$, $$y(n) = \sum_{m=1}^{M} \gamma_m \beta_m(n) + e(n). \quad (5)$$

A detailed description on how to solve the above equation, including exemplary computer code, is given in Korenberg and Hunter 1996.

Exemplary Results and Post-Processing Using Volterra Kernels

Using the techniques outlined, Volterra kernels were used to analyze experimental data from skin subjected to indentation. The input is sampled at 2 kHz and the cutoff for the input is an $8^{th}$-order Butterworth at 200 Hz. While several distributions and inputs were tested, a uniform distribution was used except where indicated and a uniform input was used because it does a better job of exploring the range of the nonlinearity than a Gaussian input. The input memory length has been shown to be around 250 samples for this sampling rate. Since this would result in an extremely long computational time, the information was initially downsampled by 3 to reduce the number of parameters and the computation time.

Figures 13A, 13B:
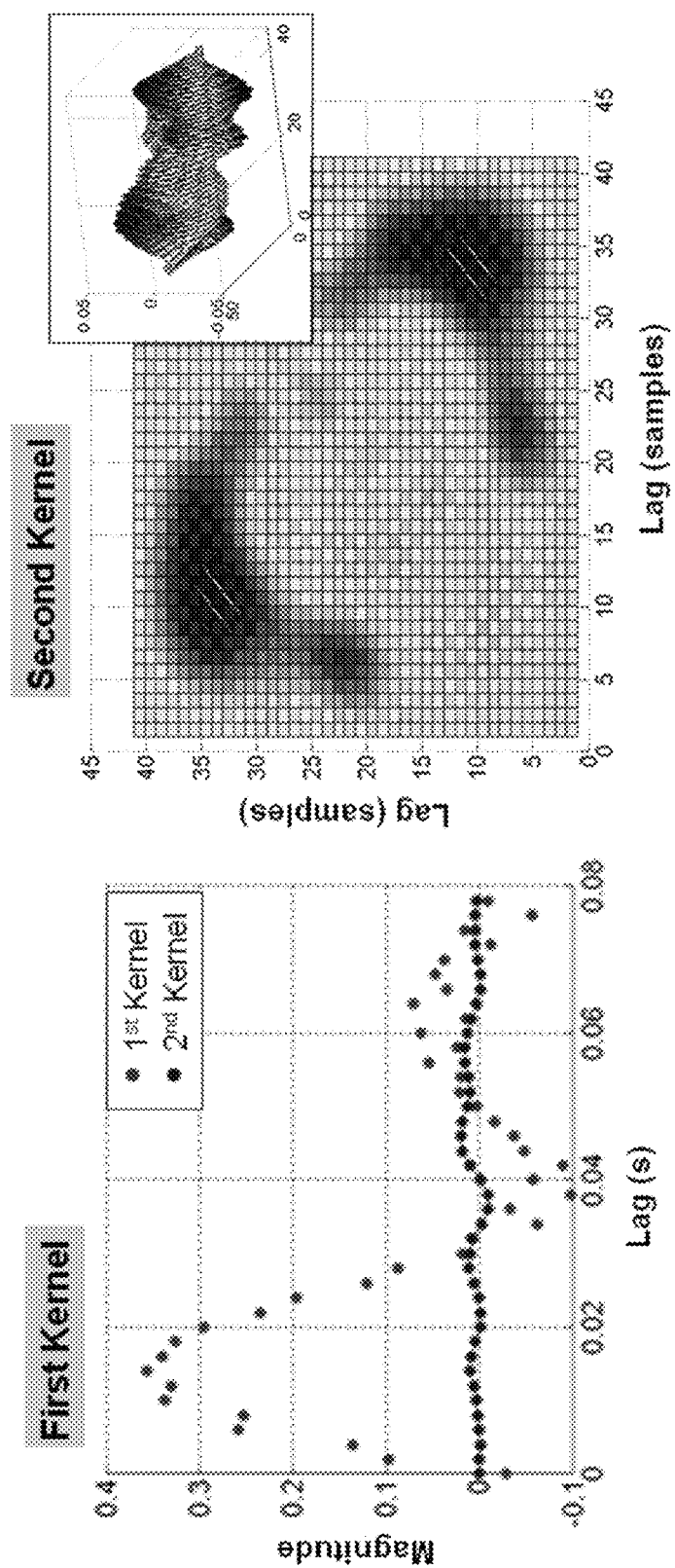
FIG. 13A shows the first order kernel and FIG. 13B the second order kernel without using noise-reducing strategies.

FIG. 13 shows plots of Volterra kernels for an example of skin measurements using an embodiment of the invention. FIG. 13A shows the first order kernel and FIG. 13B the second order kernel. Note that the Volterra kernel can be represented in terms of either samples or seconds. The first kernel, FIG. 13A, looks very much like the expected impulse response. The relative size of the first order kernel compared to the second order kernel is also shown in FIG. 13A. Most of the data can be explained by the first kernel and the first kernel has a much larger magnitude than the second kernel contribution.

The second kernel, FIG. 13B appears to have no discernible pattern. In fact, the oscillations are so violent that there are nodes of noise that go in equal magnitude towards positive values and negative values. This leaves the second kernel completely uninterpretable. It is possible to determine the estimated output by reconstructing the values of $A_m$ and $P_m$. This result shows that the VAF is very high at a value of 96% or better with a corresponding AIC of 1171.

Several methods can be used to produce smoothing in the second Volterra kernel so that it is more easily interpretable. Since the second order kernel has already been obtained, however, there are other methods that can be used to impose smoothing constraints in post-processing. With these processes, it is possible to look at the kernel before smoothing to determine if smoothing is necessary and then choose the appropriate smoothing technique afterwards. It is also possible to compare the goodness of fit before and after smoothing.

Post-Processing Techniques

Figure 14:
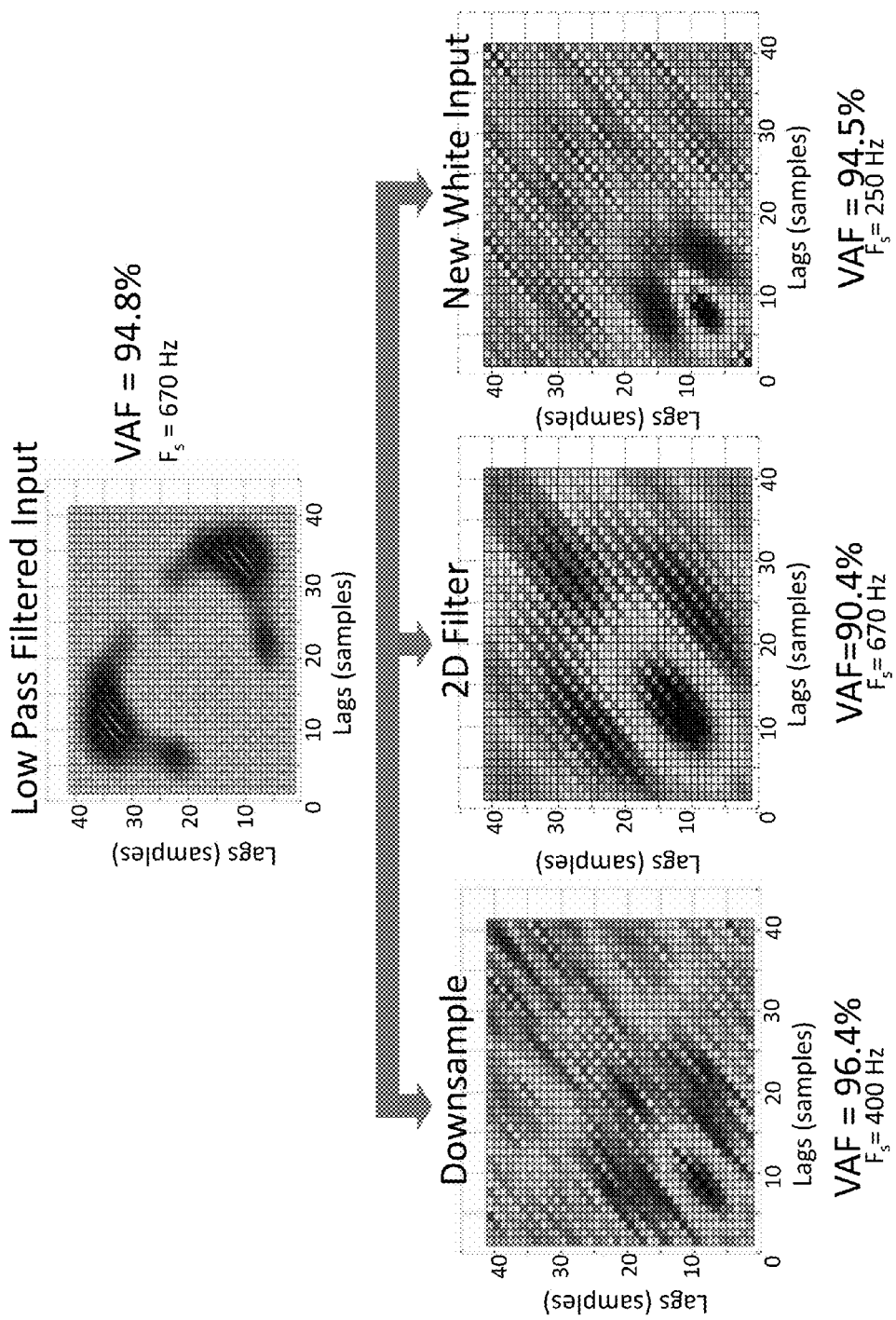
FIG. 14 illustrates three basic strategies for reducing the noise in Volterra kernels and the results on the variance accounted for (VAF) in the measured output.

FIG. 14 illustrates the three basic strategies for reducing the noise in Volterra kernels and the results on the variance accounted for (VAF) in the measured output. Post-processing techniques include downsampling, using a two dimensional smoothing filter, or using a white input signal. All of these techniques help make the second Volterra kernel more interpretable by smoothing the kernel. Downsampling is undesirable because one must downsample until the input is essentially a white input. With this technique, a lot of high frequency data is lost. In the example shown in FIG. 14, the information is downsampled by a factor of 5. A white input signal is also undesirable because it imposes a fixed structure on the input signal. A two-dimensional filtering technique (for example with a Gaussian distribution with a spread of 15 samples) is generalizable to any set of inputs and any choice of downsampling; the major disadvantage being the loss of the fitting ability of the second order kernel. For an original VAF of 94.8%, an input filter can reduce the VAF to 90.4%, downsampling can increase the VAF to 96.4% (but this is due to the fact that downsampling reduces the number of data points), and using a white signal maintains a high VAF comparable to the original as shown in FIG. 14.

By choosing post-processing techniques to look at the second Volterra kernels, it is possible to compare the original kernel with the post-processed kernel and make an informed decision about the shape of the nonlinearity. Although there are practical restrictions to the input signal for the algorithm presented, additional post-processing has helped overcome some of them. The heart of the algorithm is based on a Gram-Schmidt orthonormalization technique, which can be used to solve not only Volterra kernels but also any other type of basis function as long as certain conditions are met. There are several applications of this algorithm including different basis functions and partitioning systems.

Systems with different stiffness and damping can be compared, to first order, by comparing the relative values of different peaks in the first and second Volterra kernels. It is worth mentioning that this is a qualitative comparison and that it may be difficult for clinicians to compare these values graphically. It may therefore be desirable to be able to do a quantitative comparison with fewer parameters or using different representations.

Partitioning

Partitioning techniques are nonlinear system identification techniques based on the Gram-Schmidt orthonormalization solver described above with reference to FIG. 12 (see, e.g., Korenberg and Hunter 1996). The motivation for using a partitioning technique for stochastic system identification follows from a few desirable characteristics: short testing length, physical interpretability (easily quantitatively comparable) and flexible model structures. The concept behind the technique is to break up the input signal into groups based on a set of rules such as the output level, the direction of the signal (whether it is going in a positive or negative direction), or some fuzzy logic-based input and output rules. Then, by using direct orthonormalization as a solver, the "impulse" responses or kernels for each of these rules can be obtained.

The use of stochastic inputs is desirable because the technique queries multiple frequencies at once. When using stochastic inputs with nonlinear systems, there are several ways to approach the initial identification. In one approach, the user can use a small perturbation range since most physical systems can be linearized for small regions. This localized linear technique, however, will require multiple separate tests or will require the user to add a ramp or sine function to the stochastic signal during the test. After the test, the user will have to do linear system identification on small chunks of locally linear data. This process can be slow and it is desirable to use a faster technique, such as partitioning, that can obtain linear and nonlinear information at the same time.

Depth Dependent Partitions

The formulation for depth dependent partitions, one of the preferred embodiments, assumes a monotonic static nonlinearity and is not applicable for non-monotonic nonlinear functions. The basic idea behind this representation is that the dynamics of a system change as a function of depth into the skin and that the dynamics do not have a particular pattern that must be matched by all the constituents. For example, this means that the effective mass, damping, and spring constants, $M_e$, $B_e$, and $K_e$, do not have to evolve with the same underlying static nonlinearity. Data from different depths is loosely grouped together and an overall "impulse" response or kernel for that group is given. This is similar to the idea of completing localized linear system identifications with inputs of smaller ranges.

A key difference between this technique and simply completing localized linear system identification is that this technique imposes the separation of the different depths after the data over the entire output range is collected. This means that it can be used to artificially group non-contiguous sections of data that are collected at the same depth in order to make an estimate of the dynamics.

It is expected that the "impulse" responses from these partitioned kernels would not produce results that look exactly like the results obtained from localized linear tests. The main reason is because the localized linear techniques contain little or no data for cross dynamic terms between different depths. The depth dependent partitioning, however, does contain cross dynamic terms that will cause some averaging to occur across the kernels. In the case where there are no cross dynamic terms, however, the localized linear and depth dependent partitioning techniques would produce exactly the same results. Other more advanced types of partitioning schemes can be used to separate the cross dynamic terms.

Figure 12:
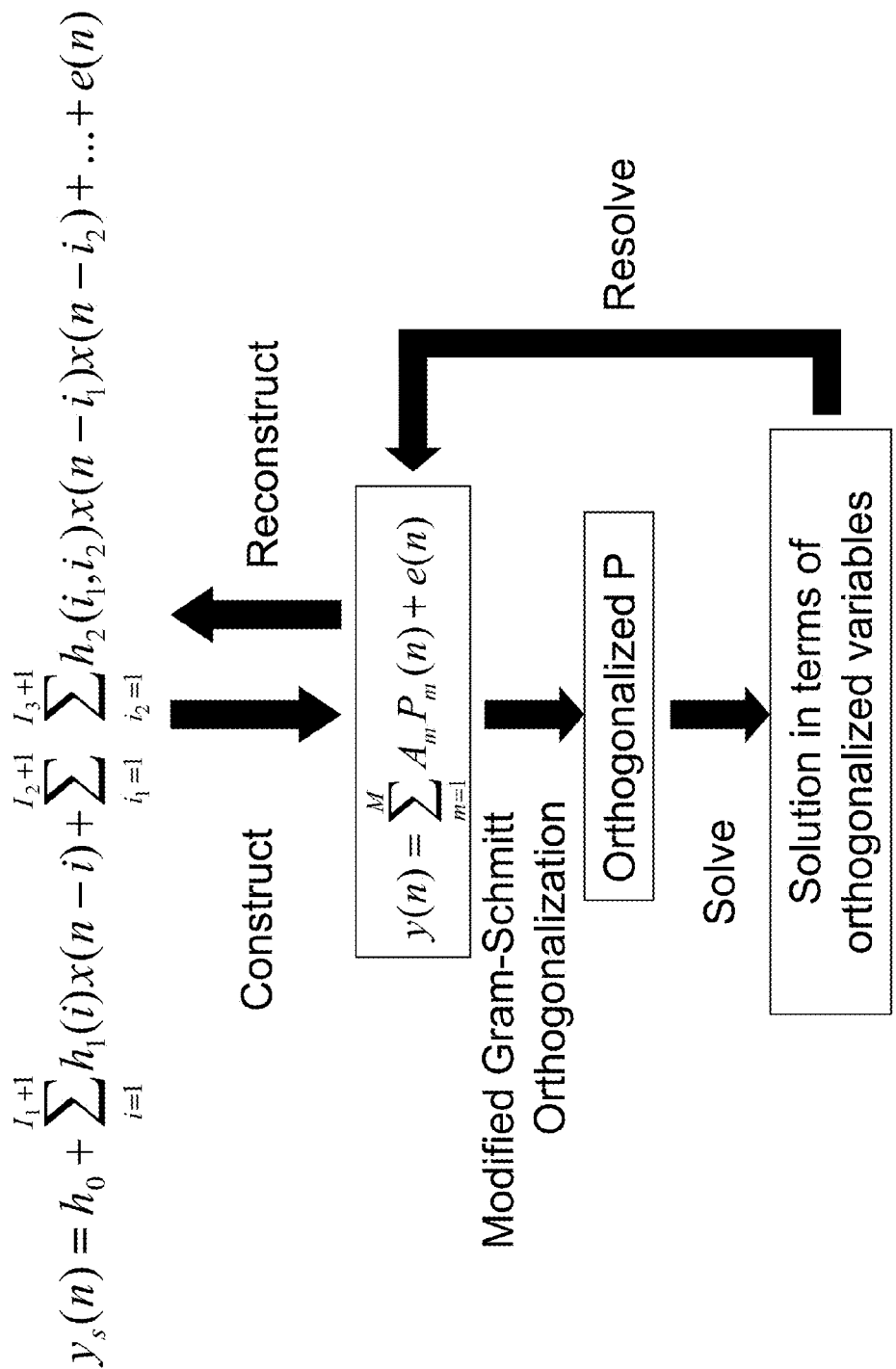
FIG. 12 illustrates an algorithm that can be used to solve for Volterra kernels. The algorithm involves constructing the kernel, orthogonalization, solving, resolving, and reconstructing.

The method used to solve for the partitioning technique involves using the Gram-Schmidt Orthonormalization technique described with reference to FIG. 12. The construction and reconstruction steps, however, are replaced by the equations listed below. The construction equation for the depth dependent partitions listed below would replace the corresponding equations for Kernel construction in Korenberg and Hunter 1996 in the solution process, $$P_m(n) = \begin{cases} 1 & \text{for } m = 1 \text{ and } n = l + 1 \ldots N \\ x(n - j + 1) & \text{for } m = 2 \ldots K_{max}(l+1). \\ & n = l + 1 \ldots N, \\ & \text{and } j = 1 \ldots l + 1 \\ & \text{when } L(k) \leq y(n - j + 1) \leq L(k+1) \\ & \text{for } k = 1 \ldots K_{max} \end{cases} \quad (6)$$

where $K_{max}$ is the total number of partitions, k is the partition counting variable and L(k) is the partition breakpoint. The most important criteria necessary for generating a partition scheme is that the construction equation must be orthogonal. This means that there cannot be overlapping segments or repetition of any segments. For stability and noise rejection, the output y used for the construction of the kernels can be low-pass filtered while they used for the solution steps are not altered.

The following equation would then be used to replace the corresponding equations for kernel reconstruction in Korenberg and Hunter 1996 in the solution process for reconstruction. This equation contains information for different partitioned kernels, each of which is similar to an "impulse" response. The total number of these kernels is equal to the number of partitions $K_{max}$, $$\hat{h}_p(i,j)=A(m) \text{ for } i=1 \ldots K_{max} \text{ and } j=1 \ldots I+1$$
$$\text{where } m=j+(i-1)(I+1). \qquad (7)$$

The number of partitions can be chosen to be any value up to the fitting limit. This means that the total number of parameters (which is equal to the number of partitions multiplied by I+1) must be at most one third of the total test length.

The partitioning breakpoints can be set based on several different criteria. The first obvious criteria would be equal partitions where each partition covers the same distance. Realistically, this means that each partition would have a different number of data points which would then cause some partitions to have too few data points for proper fitting.

Another possible partitioning breakpoint algorithm would involve choosing breakpoints such that each partition has the same number of data points within it. This avoids the problem of having too few data points in any partition but causes some averaging effect to occur. This is the type of breakpoint that is used in most of the following analysis. The algorithm used to generate these breakpoints involves putting the entire output data series in order from the lowest value to the highest value. The break points can then be chosen to split the number of data points evenly. The depth value that would correspond to this even split can then be directly chosen from the ordered series.

In the ideal case, it is best to have partitions that are equally spaced where each partition has an equal number of data points. This would mean that the ideal output distribution would have to be uniform over the test range. This type of constraint can then be used as a criterion for optimizing the selected input.

It is important to point out that the depth dependent partitioning scheme is directly dependent on the output of the system whereas the Volterra kernels were dependent on only the input. Therefore, any computational savings in the solution method for the Volterra kernel, where the input orthogonalization is pre-calculated, cannot be used. The output partitioned kernels, however, generally have fewer parameters than the Volterra kernels which means that the computation time is lower.

Exemplary Partitioning Results

Figures 15A, 15B:
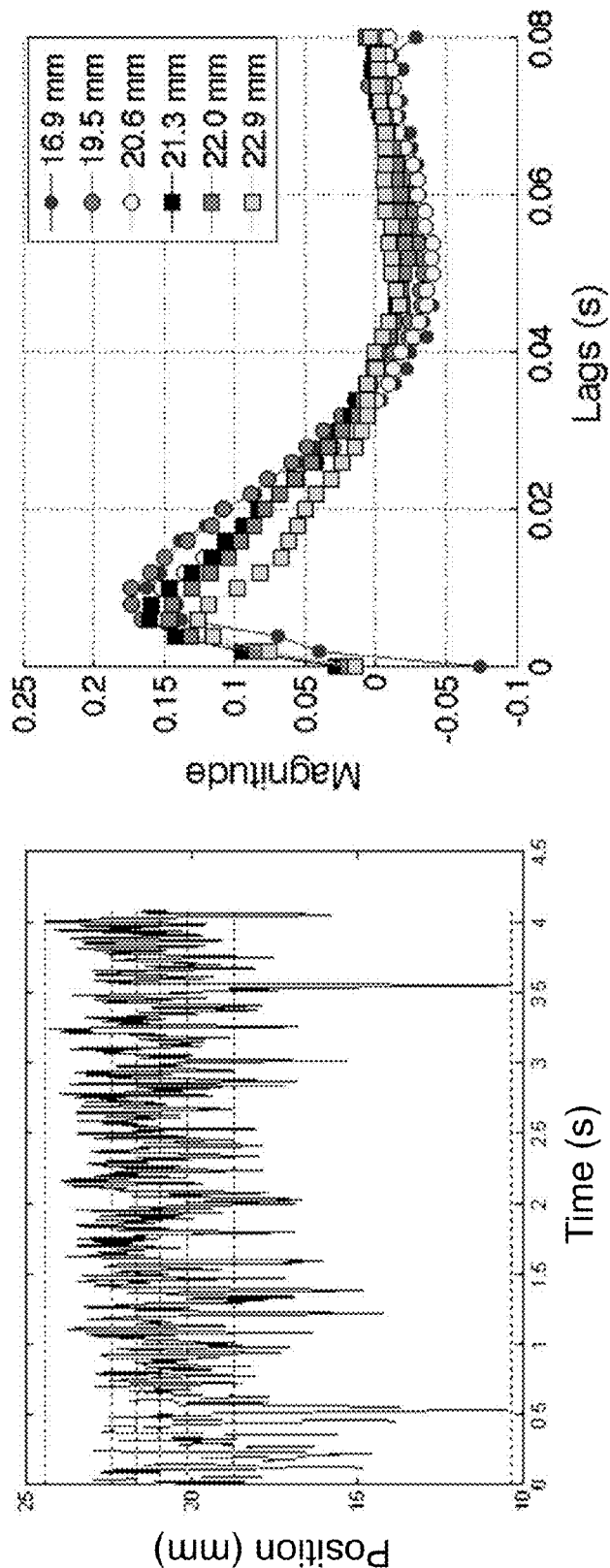
FIG. 15 illustrates an example of depth partitioned results for skin showing (A) the partitioning of the output record chosen by data density and (B) calculated kernels or "impulse" responses at different depths.

FIG. 15 illustrates an example of depth partitioned results for skin. FIG. 15A shows the breakpoints for the partitioning and FIG. 15B the kernels obtained from the estimate. The breakpoints, indicated by horizontal dashed lines in FIG. 15A, were chosen by data density so they are clustered heavily at the deeper values. Depth of indentation or position in millimeter (mm) is shown on the vertical axis in FIG. 15A. One large partition exists at the very deepest values and one large partition exists at the shallowest values.

As shown in FIG. 15B, the resulting kernels look like "impulse" responses as a function of depth. The deepest depth at 22.9 mm has a very heavily damped "impulse" response while the shallowest depth at 16.9 mm is not heavily damped and shows more of the negative oscillatory peak. Since the average value is still being estimated in the partitioned kernel, there is some coupling of all the kernels with the average value.

Comparison with the Wiener Static Nonlinearity

To assess the goodness of fit of the depth partitioning technique, the variance accounted for (VAF) and the Akaike Information Criterion (AIC), are calculated. The AIC is a method of measuring the negative impact of the entropy from additional parameters in estimation. In this data set, there are 15 partitions and the data was downsampled by 4. The estimated memory length was 40 samples. The VAF of this system is fairly good at 92.2%. This is on par with results obtained using Volterra kernels except with fewer parameters (600 parameters total for the partitioned technique versus 903 parameters for a second order Volterra with the same memory length).

Direction Dependent Partitions

A slightly more advanced technique is the direction dependent partitioning method. The idea is that as the probe moves into the skin, such as probe 102 when used in a configuration shown in FIG. 5A, it will produce different dynamics than when moving out of the skin. At low displacements near the surface of the skin, one does not expect to see this effect. At deeper positions into the skin where the compression is heavy, one expects to see a difference between the dynamics of pushing and pulling.

Linear system identification and most other nonlinear identification techniques including Volterra kernels assume no directional dependencies. There are a class of system identification techniques based on characterizing hysteresis that are capable of looking at direction dependent and history dependent dynamics. By partitioning the output, it is also possible to begin looking at the direction dependent dynamics as a function of depth. The construction equation that can be used for direction dependent partitioning is very similar to construction equation for the depth dependent, except that one must account for direction, but for example a direction parameter D. For example, D is positive for one direction and negative for the other direction. As with before, the output y that is used to construct the partitions can be low pass filtered to reduce noise. The reconstruction equation is also very similar to the depth dependent case except the number of kernels is twice as many as before since it covers both cases for D.

With these two modified equations, it is possible to identify direction dependent dynamics. The results of this can be compared to depth dependent solutions. The mass as a function of depth does not change at all between pushing into the skin and pulling off the skin at the same depth. The estimate for the damping and the spring constant, however, diverge as the probe goes deeper into the skin. This is in line with expectations since it is expected that the skin would have more damping resistance going into the skin than pulling off the skin. It is also expected that pushing into the skin produces higher stiffness estimates than pulling off the skin at the same depth.

With the results from these two different types of partitioned kernels, one is able to tease apart some components of the dynamics using data from a single test. These methods tend to have a fewer number of parameters and high VAF. In addition, they are more interpretable and easier to compare than Volterra kernels. Conceptually, they are capable of measuring more dynamic features than simple static nonlinearities. Therefore, these partitioning techniques lie between the capabilities of the Volterra kernel and the static nonlinearities. Other partitioning schemes, including frequency dependence, can be used to group data in other configurations to obtain more general nonlinear dynamic estimates.

Input Generation and Real Time System Identification

In off-line system identification techniques the input generation, the system perturbation, and the system identification are three separate events that are completed in series. In real-time system identification the system perturbation and system identification steps are completed together. Input generation can be combined with system perturbation and system identification in a single real-time algorithm.

Input Generation

Input generation is the key to stochastic system identification. For some techniques, such as for Wiener kernels, only certain input types will work. An input can be classified by its distribution (Gaussian, uniform, Rayleigh, etc. and by its spectral content (white or colored). Input signals can be generated with several different methods optimized for different situations. One type of input generation includes techniques that try to create inputs with a pre-specified distribution and spectrum (or auto correlation).

When dealing with linear systems, the selection of the optimal input is simple and either Gaussian white inputs (or colored Gaussians) or stochastic binary signals are used. For nonlinear functions, however, it is much more difficult to make a general assessment of the optimal type of input. For the types of nonlinearities found in biological tissues, where the nonlinearity is a function of the depth into the tissue, a good guess for an optimal input is an input that can generate a uniform output. A uniform output would explore the entire range of positions in the nonlinearity and provide an equal number of values for all depths. In order to generate this optimal input, however, the system nonlinearity must be known. It is possible to generate one input, assess the output, and then iteratively generate new inputs until the desired output is found. If this procedure is to be done by hand, it would require someone skilled in the art, it would be time consuming, and it would require a large number of trials. For an instrument to be used in a clinical setting, the input can be generated in real time using system feedback thereby forgoing the disadvantages of creating inputs by hand.

Real Time System Identification

Adaptive and recursive algorithms can identify a system in real time. Each additional data point obtained can be used to modify the system impulse response immediately. These techniques are valuable in situations where the system changes or degrades over time. With recursive least squares (RLS), the additional data point is used to optimally improve the overall estimate and information from all the data points is kept in the estimate. With adaptive least squares (ALS), some of the prior information is forgotten and the impulse response better reflects the most recent information. Adaptive and recursive least squares algorithms are commonly used and multiple derivations exist and are optimized for different situations.

Input Generation with System Feedback

To properly identify the features of a nonlinear system where the nonlinearity is dependent on the output parameter, it is important that sufficient information is gathered across the output range. There are several ways to achieve the optimal output that can be used to identify the system including (but not limited to):

Real time input generation (RTIG) with output probability density function (PDF) feedback: Measure the output of the system in real time and adjust the offset of the input to meet the desired output distribution or PDF.

Figure 16A:
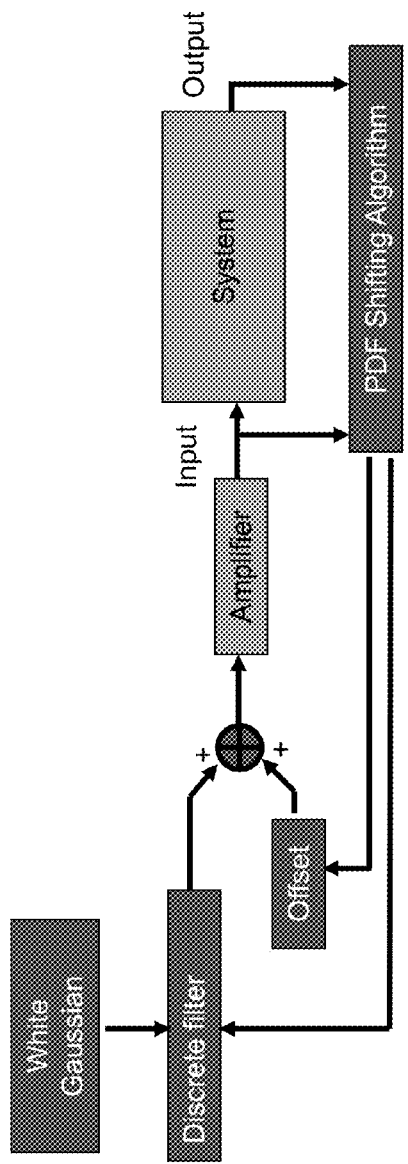
FIG. 16A illustrates a real time input generation (RTIG) scheme with output probability density function (PDF) feedback.

The optimal system output would be one in which the output distribution or PDF is uniformly distributed across a desired range for an input frequency of a sufficiently high cutoff. In order to achieve this, it is possible to add a properly filtered input range to an offset, which can be controlled to achieve the proper output range. In this strategy, it is not important to identify features of the system other than the output PDF. FIG. 16A illustrates an RTIG scheme with output PDF feedback.

Real time input generation (RTIG) with output PDF feedback and system identification: Measure and identify the system in real time and adjust the offset of the input to meet the desired output PDF.

Figure 16B:
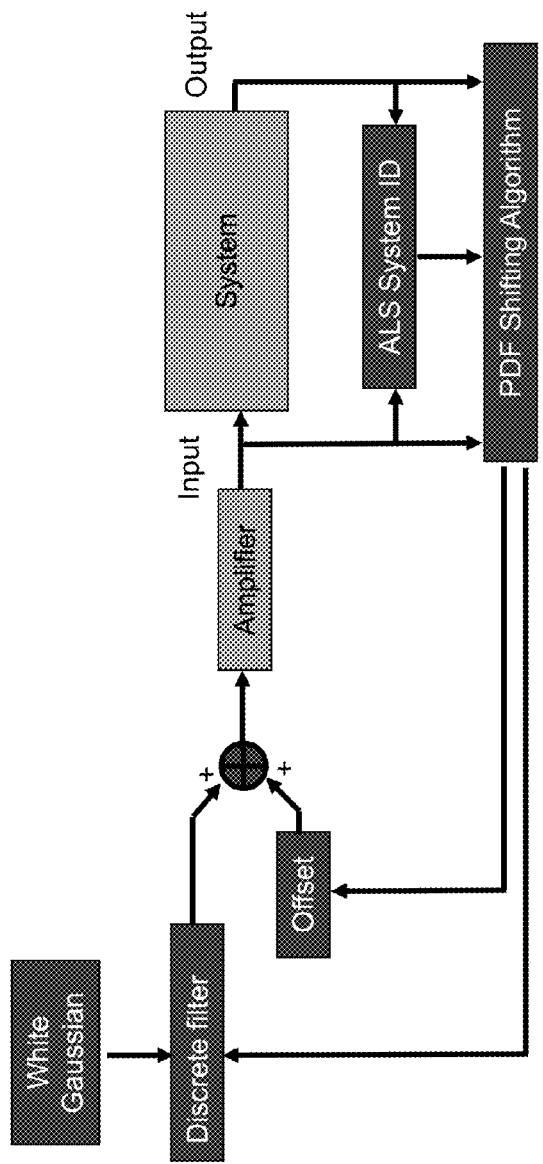
FIG. 16B illustrates a Real time input generation (RTIG) scheme with output PDF feedback and system identification (ID).

In this procedure, the system impulse response is identified and the control system for determining the input offset is modulated using a self tuning regulator with gain scheduling. FIG. 16B illustrates an RTIG scheme with output PDF feedback and system identification.

Output PDF Feedback

One of the most basic configurations for obtaining the desired output PDF in real time is shown in FIG. 16A. First, a Gaussian or uniform white input can be generated and filtered with a controllable high order discrete Butterworth filter to the desired input cutoff. This can then be added to a lower frequency control input that is commanded via a feedback loop. Information about the output distribution can be used to increase or decrease the mean offset of the input in order to explore different locations of the nonlinearity in the output. For the PDF shifting algorithm, it is necessary to know three things about the system: the desire input range, the desired output range, and the minimum system memory length. The desired input and output ranges are used to bound the input and output to ensure that the system does not go beyond physical limits.

The minimum system memory length is used as the feedback rate. Since the input of the system is a stochastic signal with an offset, the output of the system will have a mean value that is directly related to the input offset if the rate over which the mean is being taken is longer than the minimum system memory length. If the feedback rate is faster than the minimum system memory length, the relationship between the input offset and the output mean begins to break down and the RTIG system can become unstable. In addition, to reduce the computational load for real-time input generation, a slower feedback rate is better. On the other hand, it is desirable to keep the test length short so a reasonably high feedback rate is required. In practice, a minimum memory length of 0.025 seconds (or 50 samples for a sampling rate of 2 kHz) can be used for feedback control.

The control system for the PDF shifting algorithm shown in FIG. 16A includes the following steps during each feedback loop (once every 50 samples for a sampling rate of 2 kHz):

1. First, split the output range into a number of bins. Output positions that have already been explored can be placed in these bins. The desired output distribution function is a uniform so in order to explore all the bins evenly, the desired output for the next cycle would be the one which coincides with the bin with the least number of entries. This desired location can be called y*. This idea can also be extended to other probability distributions by simply subtracting the entries from bins already filled with the desired distribution and finding the bin with the largest number of entries.

2. Next, determine the current output mean in terms of the number of bins y.

3. Modulate the other input parameters:

(a) Determine the overall gain to the system: This parameter $G_o$ can determined from a general idea of the system stiffness or memory length.

(b) Determine the edge modulation: Uniform distributions have sharp edges. This requires that the gain be decreased as the output approaches these edges. Depending on the location of desired output location y* and the current output location y, it is possible to increase or decrease the overall feedback gain using the edge modulation parameter $E_m$.

(c) Determine the stochastic input S(t): For a desired PDF with sharp edge contrast like a uniform distribution, it is generally a better idea to use a uniform stochastic input. Otherwise, a Gaussian distribution will also work.

(d) Determine filter F(·) and gain $G_s$ the stochastic input: Larger gains will obtain more information about the system but can also cause instability. The gain $G_s$ can be scaled up to about 20 to 30% of the total input range and remain stable. The input filter is not necessary for algorithm functionality but can be implemented to clean up the signals.

4. Combine the input with the following formula where x(t) is the new input.

$$x(t)=x_o+G_oE_m(y^*-y)+G_sF(S(t)) \quad (8)$$

The first term $x_o$ is the old input offset while the second term is the offset change. The last term is the stochastic input. This configuration with the old input offset included in the output works well when the system input and output are not zero mean. Additional derivative or integral terms can be added to speed up the response of the system although additional speed could cause instability if the output mean can no longer be mapped to the input offset.

This algorithm can be improved with an identification step where the gain $G_o$ is changed depending on the system stiffness. However, to obtain an output with the desired PDF, it is not necessary to identify the system as long as the nonlinearity in the stiffness does not vary heavily. In addition, by not identifying the system, it is possible to obtain computational savings.

Using the output PDF feedback scheme shown FIG. 16A, simulation results for the input and output time series can be obtained, for example, using a linear system, a Wiener static nonlinear system, and a dynamic parameter nonlinearity (DPN) system. For exemplary results, the output range was constrained to vary between 0 and 6 mm and the input range was allowed to vary from −5 to 25 N.

Figures 7A, 7B:
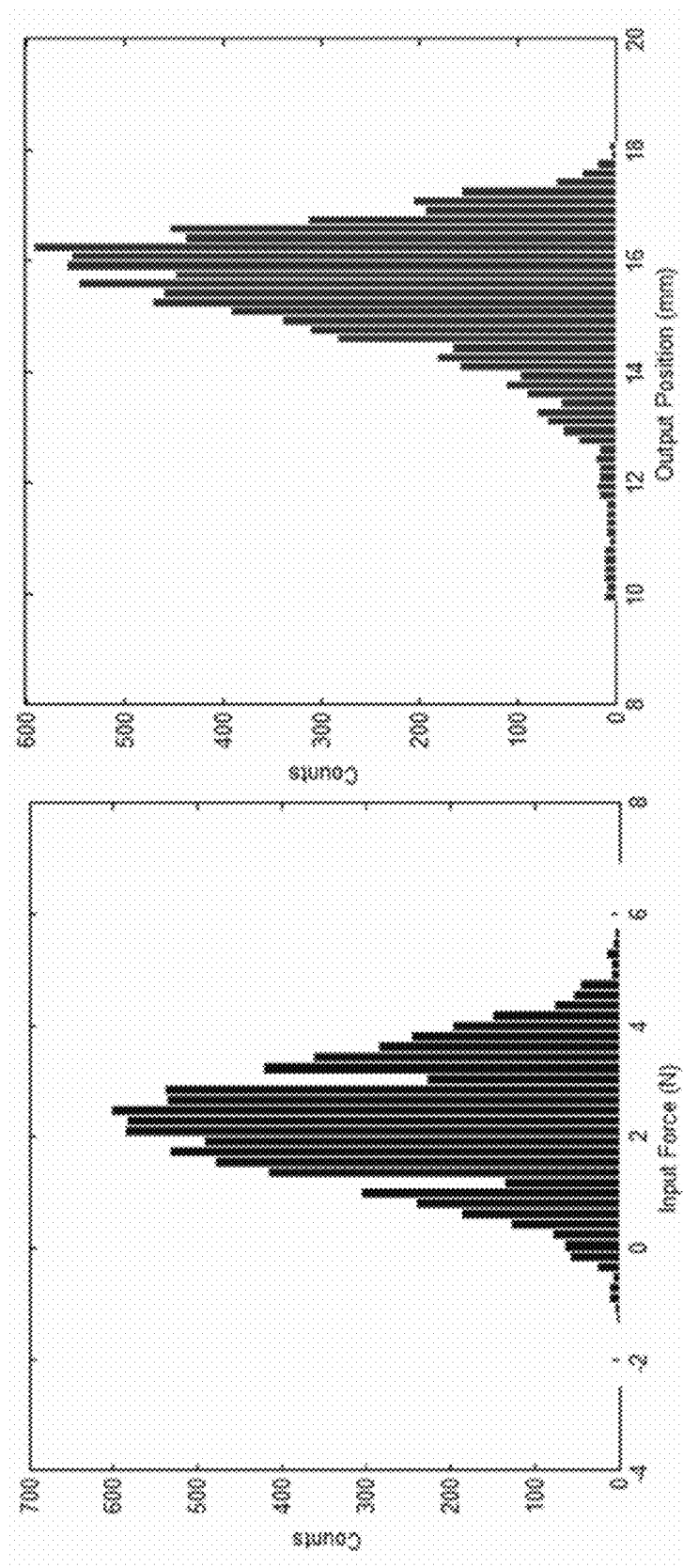
FIG. 7A shows an example of an input force distribution and FIG. 7B the corresponding output position distribution for skin under indentation perturbation.

The algorithm is controlled by the output PDF, such as that shown in FIG. 7B, which can be analyzed. The linear system shows the ideal output PDF that is very close to a uniform shape between 0 and 6 mm with sharp edge features. The Wiener and DPN systems, however, have shifted probability distribution functions. The main reason for this is that the underlying nonlinearities in these two models have a variation in stiffness for deeper positions. If the bin with the least number of entries is near the stiffer regions, more and more input force is necessary to reach that depth. Since the stiffness is unknown, the algorithm does not adapt to increase gain for these stiffer locations and therefore takes a longer time to reach those regions. Therefore, more entries occur in stiffer regions. Although the resulting distribution is not ideal, it is still possible to control the input and output ranges with this algorithm.

The real time input generation scheme described herein has one additional interesting feature. Since the cyclic behavior is slow, the resulting predictions from the static nonlinearity are not as accurate. The static nonlinearity for the Wiener system is scattered and noisy. The static nonlinearity plot for the DPN system, on the other hand, is very narrow and does not exhibit the effects of the cross dynamic terms since the output did not travel across large ranges fast enough.

Despite these drawbacks, the real time input generation without system identification works well for linear systems and systems with small variations in stiffness. The algorithms are also relatively fast and can be completed in 1.3 seconds for a 5 second test making it a viable candidate for real time input generation.

Output PDF Feedback with System Identification

When the identification is performed in real time, as is the case with the recursive lease squares (RLS) and adaptive least squares (ALS) techniques, the identified system can only approach the optimal solution. If the goal is to identify the system, then an ALS algorithm can be used with some modification in conjunction with a real-time input generation scheme. This idea is shown in FIG. 16B where the data acquisition and identification steps are connected directly to the input generation step. This methodology is distinct from the idea of using an observer since the observer poles must be faster than the system poles. With this method, the feedback poles must be much slower than the system poles.

This scheme is similar to the above-described PDF feedback scheme except for the additional system identification step using an ALS algorithm. This algorithm utilizes information about the identified system to determine the optimal input gains. The ALS system identification (ID) block, FIG. 16B, functions as follows once every feedback cycle:

1. Add new input and output sequences to an ALS algorithm. Note that including the ALS algorithm may cause the RTIG system to go unstable if the ALS algorithm itself is unstable due to the choice of the identification memory length (which does not have to be the same size as the feedback memory length), impulse response fitting functions or the change factor. The ALS system will adapt as the system goes to different regions of the output nonlinearity.

2. Fit the most current impulse response to determine the stiffness, damping, and mass and associate these values with the average local bin position. This step can be the most computationally intensive and time consuming and will increases the total computation time to 7.5 seconds for a 5 second test. This, however, can be easily shortened by decreasing the number of parameters over which the fit is conducted or trading of fitting accuracy for speed.

3. Scale the gain $G_o$ and other input parameters with the identified system parameters at the average local bin position. The simplest version of this can be done by scaling the input gain directly with the identified local stiffness. More complex methods like pole placement can also be used. This database of input parameters that depend on the local bin position can be passed on to the PDF shifting algorithm.

Exemplary results based on this algorithm show an immediate improvement in the cycling time which can be as low as 0.2 seconds for all the systems marking an improvement in the time necessary to identify the nonlinear system. The plateau periods are also shorter and less pronounced. Improvements also appear in the output PDF.

For example, when system identification is not used, it was only possible to achieve a uniform PDF for the linear system. With the addition of depth dependent system identification via the ALS algorithm, it was possible to achieve near uniform PDFs for the same Wiener static nonlinearity and dynamic parameter nonlinearity (DPN) systems. In addition, since the cycling speed increased, cross dynamic terms start to become visible in the static nonlinearity plot of the DPN system. The static nonlinearity plot of the Wiener system, such as the one shown in 10B, also becomes better defined.

Figure 17:
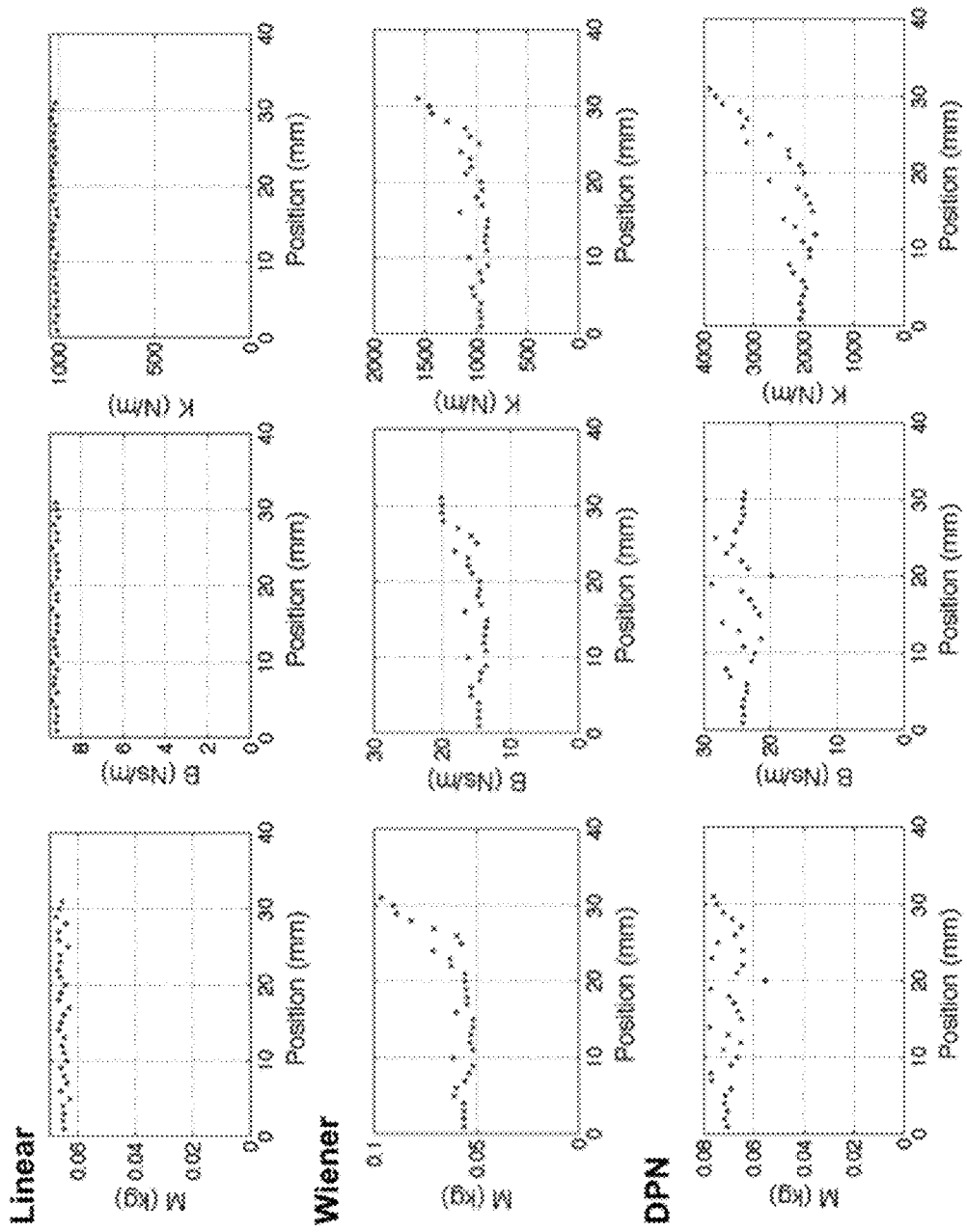
FIG. 17 shows identified parameters from real time input generation with PDF feedback and adaptive least squares (ALS) algorithm. Three different systems, a linear system, a Wiener static nonlinear system, and a dynamic parameter nonlinearity (DPN) system are shown.

The values from the ALS can also be used to identify the depth dependent parameters of the system. FIG. 17 shows identified parameters from real time input generation with PDF feedback and adaptive least squares (ALS) algorithm. Results for three different systems, a linear system, a Wiener static nonlinear system, and a dynamic parameter nonlinearity (DPN) system are shown. The parameters mass M, damping B, and stiffness K, are plotted as a function of position, or depth, of the skin indentation. The linear system shows no variation in the three parameters as a function of depth. The Wiener system shows how the three parameters of mass, damping, and spring constant all change with depth in the same fashion. The DPN model shows how the three different parameters can vary differently with depth.

There are two general caveats to using the ALS algorithm for system identification in this case. First, since the stochastic input range is large, a lot of averaging across depths can occur which may skew the parameter estimates by averaging across depths. The ALS algorithm itself may additionally skew estimates across time. Better estimates may therefore be obtained from the input and output data if an additional offline system identification technique is used after the data has been gathered.

Example Skin Studies—Indentation

Using a desktop version of device 100, the left anterior forearm 40 mm from the elbow and the left posterior forearm 40 mm from the wrist were tested for 7 right handed males between the ages of 18 and 28. Five measurements were taken at each location using the same stochastic input.

Figure 18:
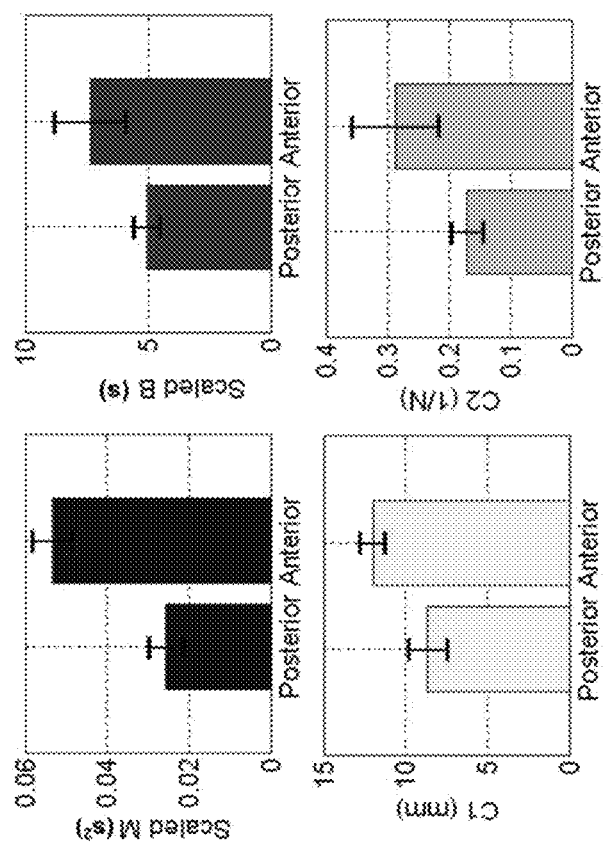
FIG. 18 shows plots of the means and standard deviations of four mechanical properties of skin for two different positions on the left arm.

FIG. 18 shows plots of the means and standard deviations of four mechanical properties of skin for two different positions on the left arm. This figure shows significant differences across all four metrics, which are scaled mass M, scaled damping B, non-linear constant $C_1$, and non-linear constant $C_2$. Variation between individuals is more than ten times the variation between measurements for the same individual. In FIG. 18, the anterior position generally has a lower spring constant which boosts the scaled mass and the scaled damping. In addition, the anterior position has a larger compressible depth, which boosts estimates of $C_1$ and $C_2$. The means, standard deviations and the p-value from an ANOVA study are shown in Table 1.

TABLE 1

Linear and nonlinear parameters and p-values of the left anterior and posterior forearms of male, right-handed subjects.

| Quantity | Anterior Forearm | Posterior Forearm | P-value |
|---|---|---|---|
| Scaled Mass (s2) | 0.0256 ± 0.0042 | 0.0532 ± 0.0048 | <0.0005 |
| Scaled Damping (s) | 5.02 ± 0.57 | 7.35 ± 1.49 | 0.002 |
| Nonlinear Constant C1 (mm) | 8.66 ± 1.03 | 11.99 ± 0.79 | <0.0005 |
| Nonlinear Constant C2 (1/N) | 0.170 ± 0.023 | 0.287 ± 0.069 | 0.001 |

Note the normalized parameter estimates differ from the effective parameter estimates because the normalized parameters are achieved by dividing the impulse response by the DC compliance. This fixes the normalized spring constant at 1000 N/m. The p-values show that the linear and nonlinear constants are significantly different for the two positions demonstrating that the device can easily differentiate between the tissue properties at one site from those at another. In this table, all the metrics are statistically significant with p-values that are much less than 5%.

The posterior forearm has more damping as well as a larger compressible depth, which are characteristic of more compliant tissue. The depth-dependant stiffness in the skin ($C_1$ and $C_2$) can be used to determine parameters needed for needle free injection or used as a measure of skin elasticity, which has been studied for applications in cosmetics.

Device 100 can also be used to study larger populations of subjects to analyze subgroups based on demographic similarities, such as age, gender, height, and weight. The device may be used to identify parameters that provide indicators for body mass index (BMI) and help identify similarities across the population.

Example Skin Studies—Extension

Figures 19A, 19B:
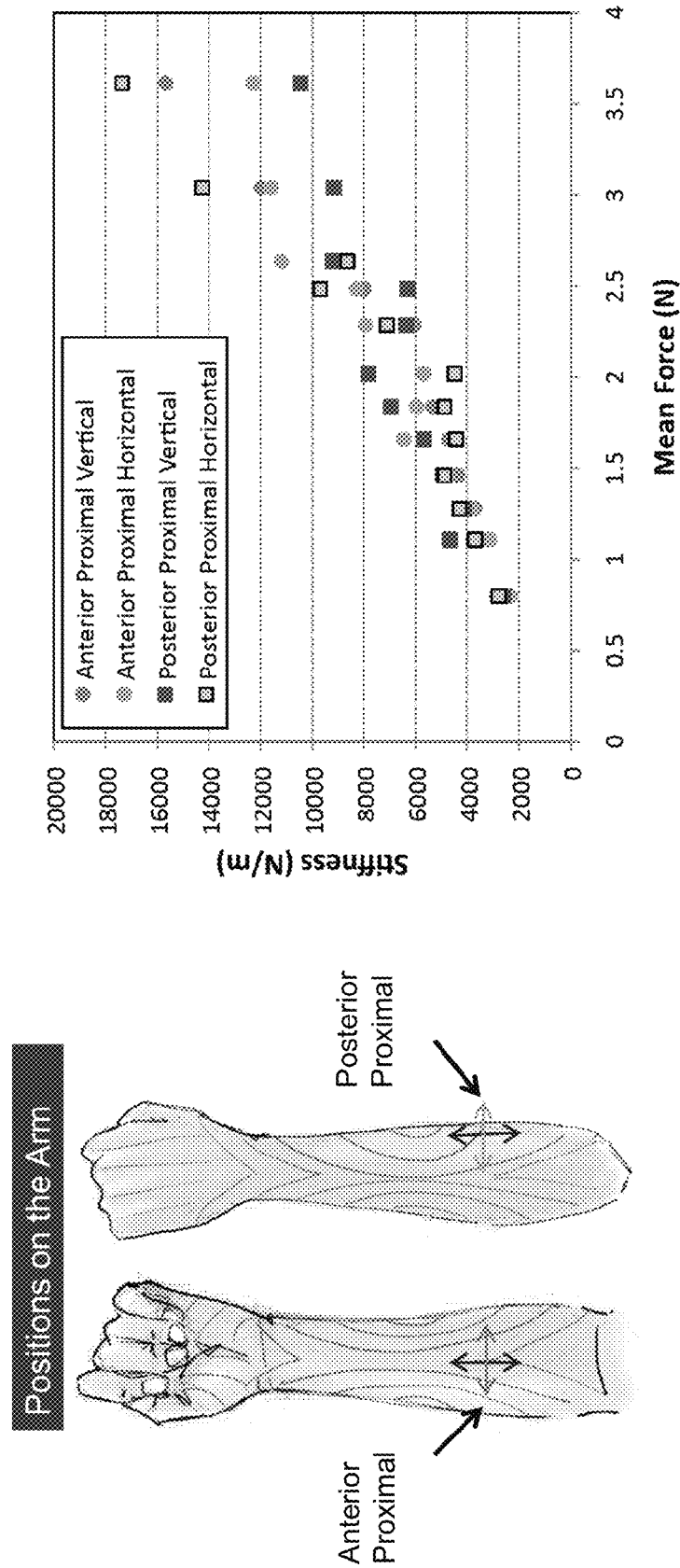
FIG. 19A illustrates two locations on the skin tested with extension perturbation.
FIG. 19B shows skin property measurements obtained at the locations illustrated in FIG. 19A.

Conventional extension is done in vitro but can also be conducted in vivo. With an embodiment of the invention, such as device 100, two positions on the skin were tested including the anterior proximal position and posterior proximal position 40 mm from the elbow as shown in FIG. 19A. Such tests can be performed to determine the orientation of Langer's lines, which are indicated schematically as thin lines in FIG. 19A. The initial length of the area being tested was consistent for all four configurations. The vertical and horizontal directions were tested and the localized linear results are shown in FIG. 19B. For lower forces, there does not appear to be a preferential alignment of the stiffness of skin in a particular orientation. As the forces increase however, preferential alignment or increased stiffness begins to appear in the orientation of the Langer's lines in those regions. For the anterior proximal location, the vertical orientation is stiffer than the horizontal orientation at larger forces. For the posterior proximal location, the horizontal orientation is stiffer. These results are in line with expectations with higher stiffness or tension in the direction parallel to the Langer's lines.

Example Skin Studies—Surface Mechanics—Skin Care products

The surface mechanics of skin includes several properties including skin texture, suppleness, and friction. When a probe, such as probe shown in the inset of FIG. 5C, is placed on the skin, the skin can deform contributing to changes in the measured damping (from skin energy absorption, skin friction and other factors) as well as the spring constant (from skin suppleness, skin stiffness and other factors). It is possible to measure the change in the spring constant of the skin as well as the damping using the surface mechanics probe configuration of device 100.

Commercial products such as hydrating lotions claim that they help hold moisture in the skin. Two different products with two different hydrating strategies were tested. The CHANEL HYDRAMAX+ACTIVE brand product is a non-greasy hydrating lotion which creates a protective layer on the skin. The VASELINE TOTAL MOISTURE brand cream is a more viscous mixture. First, indentation studies were conducted using device 100 with the localized linear method at different depths into the skin. A baseline measurement of the mechanical properties of skin was first collected using device 100 in an indentation configuration. An hour later, one of the lotions was applied and the skin was tested again. Once a lotion was applied, the skin was allowed to rest for more than one day before any further testing. The results of the indentation tests are shown in FIG. 20.

Figure 20:
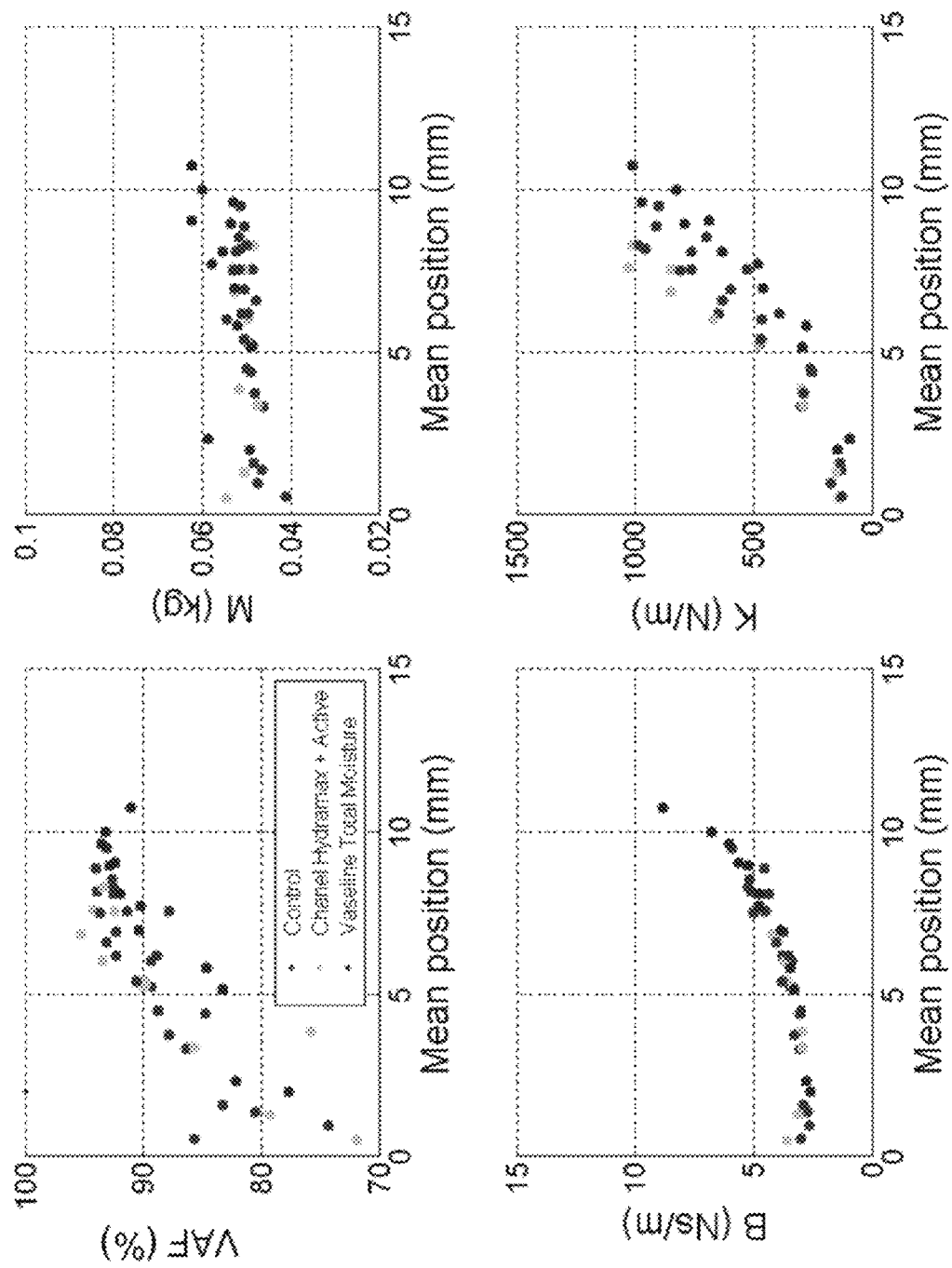
FIG. 20 shows results from skin surface mechanics testing using indentation with and without lotions applied to the surface.

As shown in FIG. 20, there may be small differences between the use of different lotions and the control baseline. There is no significant difference in the mass M or the damping B, but there is a spread in the spring constant K.

With the CHANEL brand product, the spring constant of the skin actually increased slightly so that the skin became firmer. For the VASELINE brand product, the skin became softer and the spring constant was lower for every depth tested.

Figures 21A, 21B:
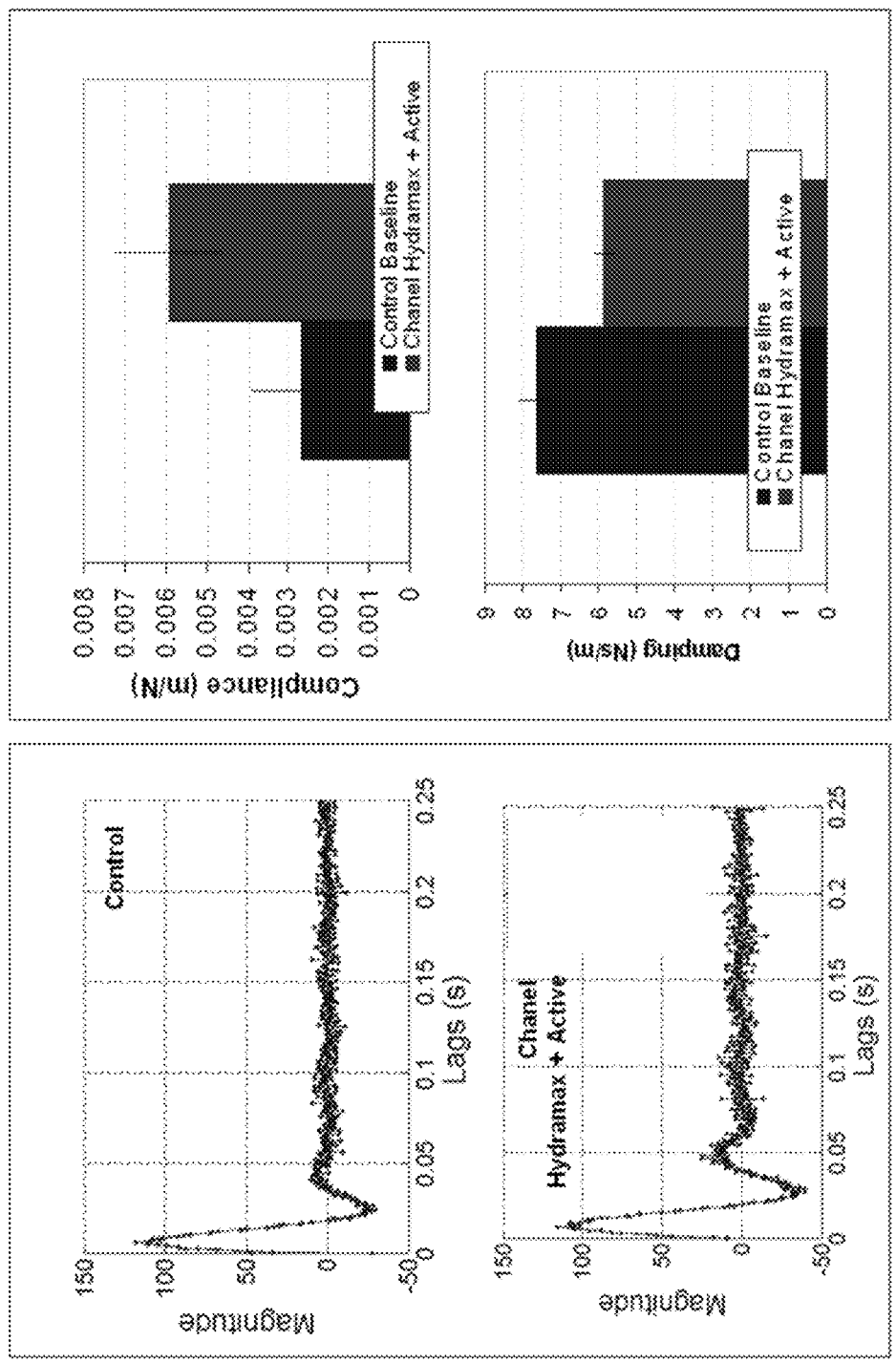

In terms of assessing the CHANEL brand product, however, an indentation test may not be as useful as other testing configurations. The major effect of the product is to generate a hydrated layer in the skin, which can be characterized by a change in smoothness or in the surface mechanics. Therefore, a surface mechanics test can be conducted using an embodiment, such as device 100, after applying the product on the skin. In an example surface mechanics measurement, the normal preload is 1 N. The dimensions of the probe in the example are 5 mm by 16 mm with an edge radius of 1.5 mm. The results of the example surface mechanics test are shown in FIG. 21. Each test was conducted ten times and the means and standard deviations are shown.

The spring constant of the mechanical spring used in the system was subtracted from the measurement of the compliance. Therefore, the remaining compliance is only the contribution of the skin, as measured in a surface mechanics geometry by sliding a probe 102, such as shown in FIG. 5C, across the skin surface. FIG. 21 shows that a device, such as device 100, used with a nonlinear identification technique described herein was able to detect and quantify a difference between the compliance of the skin before and after the product was applied. The CHANEL brand product made the skin more compliant in the sliding direction, which means that the skin surface would appear to be smoother and suppler. In addition, the CHANEL brand product reduced the damping of the skin, which indicates that it significantly reduced the roughness or friction of the skin at the surface.

Embodiments of the invention, such as device 100, may be used to conduct long term testing with other types of products to fully assess the effect of different lotions and creams immediately after application and a few minutes or hours after application. The data shown in FIG. 21, however, show that device 100 is consistent and sensitive enough to measure differences that can be felt by touch or palpation. In addition, device 100 can provide a clear quantitative assessment of skin properties that can be compared directly.

The devices and methods disclosed herein can identify dynamic compliance of tissue and identify nonlinear dynamics of tissue using stochastic techniques, for example, using a Wiener static nonlinearity, localized linear testing, Volterra kernels, and partitioning techniques. In addition, the identification may be optimized with input generation techniques. Other nonlinear system identification techniques, such as wavelets, subspace methods, and fuzzy logic models may also be used.

Embodiments of the invention provide an identification and computational technique that is fast (e.g., on the order of 2 to 7 seconds), good at accounting for variances in the data (e.g., VAF of more than 95%), readily interpretable, and capable of producing results that are repeatable and specific. In addition, device 100 may be used to distinguish the change in skin properties, such as compliance, after dehydration or after application of skin care or beauty care products.

Embodiments of the invention, such as device 100, are able to assess dynamic data to obtaining a more complete picture of tissue properties. In order to assess dynamic properties, a high bandwidth actuator system can be used. For example, a skin property identification geometry that is conducive to high bandwidth actuation is indentation using a probe coupled to Lorentz force linear actuator.

The device 100 provides a platform technology for easy incorporation of multiple application heads (indentation, extension, surface mechanics) in order to measure multiple tissue parameters in several directions. Preferably, device 100 has a stroke of 32 mm and the capability of driving at least 15 N of force at a high bandwidth in order to measure the nonlinear properties of skin in different configurations. To achieve these metrics, custom linear Lorentz force actuators can be used. For clinical applications, device 100 can have a hand-held form factor that is under 30 mm in diameter and 100 mm in length for the applicator body and may include integrated electronics. The design of device 100 may include the use of low cost materials and scalable designs that can easily lead to mass production, thereby making the technology readily applicable to commercialization.

Embodiments of the invention, such as device 100, can include integrated power and sensor electronics with custom software, which can be used to calibrate the system and assess the biological properties of skin and other biological tissues. Additional sensors capable of measuring non-mechanical properties of skin such as blood reflow (using a light source and sensor), water content (using electrical contacts) and tissue layer thickness (using ultrasound techniques) may be included.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A device for measuring a mechanical property of a tissue, the device comprising:
   a probe configured with a probe surface for contacting a surface of the tissue;
   an actuator coupled to the probe for moving the probe laterally with respect to the surface of the tissue;
   a detector configured to measure a response of the tissue to the lateral movement of the probe; and
   a controller coupled to the actuator and the detector, the controller configured to move the probe laterally with respect to the surface of the tissue by driving the actuator using a stochastic sequence and determine the mechanical property of the tissue by using the measured response received from the detector when the stochastic sequence is driving the actuator.

2. The device of claim 1, wherein the actuator is a Lorentz-force actuator.

3. The device of claim 1, wherein the mechanical property is indicative of tissue compliance.

4. The device of claim 1, wherein the mechanical property is indicative of tissue elasticity.

5. The device of claim 1, wherein the detector comprises a force sensor for detecting force of the lateral movement.

6. The device of claim 5, wherein the force sensor comprises a current sensor for detecting a current input to the actuator.

7. The device of claim 1, wherein the detector comprises a position sensor for detecting displacement of the tissue surface.

8. The device of claim 1, wherein the controller is configured to employ system identification to determine the mechanical property of the tissue from the measured response to the stochastic sequence driving the actuator.

9. The device of claim 8, wherein said system identification is nonlinear system identification.

10. The device of claim 8, wherein the stochastic sequence is a Gaussian input.

11. The device of claim 8, wherein the stochastic sequence is a Brownian input.

* * * * *